US011878002B2

(12) United States Patent
Kashyap et al.

(10) Patent No.: US 11,878,002 B2
(45) Date of Patent: *Jan. 23, 2024

(54) METHODS AND MATERIALS FOR USING *RUMINOCOCCUS GNAVUS* OR *CLOSTRIDIUM SPOROGENES* TO TREAT GASTROINTESTINAL DISORDERS

(71) Applicants: Mayo Foundation for Medical Education and Research, Rochester, MN (US); The Regents of the University of California, Oakland, CA (US)

(72) Inventors: Purna C. Kashyap, Rochester, MN (US); Michael Fischbach, Portola Valley, CA (US); Brianna B. Williams, Oakland, CA (US)

(73) Assignees: Mayo Foundation for Medical Education and Research, Rochester, MN (US); Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/225,513

(22) Filed: Apr. 8, 2021

(65) Prior Publication Data
US 2022/0062235 A1 Mar. 3, 2022

Related U.S. Application Data

(63) Continuation of application No. 16/388,405, filed on Apr. 18, 2019, now Pat. No. 10,993,930, which is a continuation of application No. 15/235,782, filed on Aug. 12, 2016, now Pat. No. 10,300,043.

(60) Provisional application No. 62/204,270, filed on Aug. 12, 2015.

(51) Int. Cl.
*A61K 31/405* (2006.01)
*A61K 35/742* (2015.01)
*A61K 35/741* (2015.01)
*A61K 35/74* (2015.01)
*A61K 35/00* (2006.01)

(52) U.S. Cl.
CPC .......... *A61K 31/405* (2013.01); *A61K 35/74* (2013.01); *A61K 35/741* (2013.01); *A61K 35/742* (2013.01); *A61K 2035/115* (2013.01); *Y02A 50/30* (2018.01)

(58) Field of Classification Search
None
See application file for complete search history.

(56) References Cited

U.S. PATENT DOCUMENTS 5,766,879 A   6/1998  Gerald et al.
6,331,401 B1  12/2001 Gerald et al.
2008/0241226 A1  10/2008 Abeln et al.
2009/0325949 A1  12/2009 Barlow et al.
2016/0000837 A1  1/2016  Rey et al.

FOREIGN PATENT DOCUMENTS

WO    WO 2006/029389       3/2006
WO    WO-2012142605 A1 * 10/2012 ........... A23L 1/3014

OTHER PUBLICATIONS

Bell, "Treatment with gentamicin monitored by serum antibiotic assay," Med J Aust., 2(13):481-484, Sep. 25, 1976.
Bhattacharjee and Snell, "Pyridoxal 5'-phosphate-dependent histidine decarboxylase. Mechanism of inactivation by alpha-fluoromethylhistidine," J Biol Chem., 265(12):6664-6668, Apr. 25, 1990.
Bianchetti et al., "Effects of tyramine on blood pressure and plasma catecholamines in normal and hypertensive subjects," Klin Wochenschr., 60(9):465-470, May 3, 1982.
Burkhard et al., "Structural insight into Parkinson's disease treatment from drug-inhibited DOPA decarboxylase," Nat Struct Biol., 8(11):963-967, Nov. 2001.
Fenalti et al., "GABA production by glutamic acid decarboxylase is regulated by a dynamic catalytic loop," Nat Struct Mol Biol., 14(4):280-286, Epub Mar. 25, 2007.
Gaddum, "Tryptamine receptors," J Physiol., 119(2-3):363-368, Feb. 27, 1953.
Gallagher et al., "Refined structure of the pyruvoyl-dependent histidine decarboxylase from Lactobacillus 30a," J Mol Biol., 230(2):516-528, Mar. 20, 1993.
GenPept Accession: EDU35915, "pyridoxal-dependent decarboxylase domain protein [Clostridium sporogenes ATCC 15579]," Aug. 15, 2012, 3 pages.
GenPept Accession: WP_004612385, "Multispecies: glutamate decarboxylase [Clostridiales]," Jun. 9, 2014, 1 page.
GenPept Accession: WP_007718072, "glutamate decarboxylase [[Clostridium] asparagiforme]," May 26, 2013, 1 page.
GenPept Accession: YP_006429963, "PLP-dependent enzyme, glutamate decarboxylase [Desulfitobacterium dehalogenans ATCC 51507]," Dec. 17, 2014, 2 pages.
GenPept Accession: ZP_02040762 (GI No. 154503702), "hypothetical protein RUMGNA_01526 [Ruminococcus gnavus ATCC 29149]" Nov. 9, 2010, 1 page.

(Continued)

*Primary Examiner* — Brian Gangle
(74) *Attorney, Agent, or Firm* — Fish & Richardson P.C.

(57) ABSTRACT

This document provides materials and methods related to bacterial compositions containing at least one bacterial organism having tryptophan decarboxylase activity. For example, bacterial compositions containing at least one bacterial organism having tryptophan decarboxylase activity and methods for using such bacterial compositions to improve gastrointestinal epithelial function and/or to treat gastrointestinal disorders are provided.

8 Claims, 18 Drawing Sheets
Specification includes a Sequence Listing.

(56) References Cited

OTHER PUBLICATIONS

GenPept Accession: ZP_05855305, "putative aromatic-L-amino-acid decarboxylase [Blautia hansenii DSM 20583]," Nov. 27, 2012, 2 pages.
Gershon and Tack, "The serotonin signaling system: from basic understanding to drug development for functional GI disorders," Gastroenterology, 132(1):397-414, Jan. 2007.
Giardina et al., "Open conformation of human DOPA decarboxylase reveals the mechanism of PLP addition to Group II decarboxylases," Proc Natl Acad Sci U S A., 108(51):20514-20519, Epub Dec. 5, 2011.
Goldszmid et al., "The price of immunity," Nat Immunol., 13(10):932-938, Epub Sep. 18, 2012.
Hayashi et al., "Pyridoxal 5'-phosphate-dependent histidine decarboxylase. Inactivation by alpha-fluoromethylhistidine and comparative sequences at the inhibitor- and coenzyme-binding sites," J Biol Chem., 261(24):11003-11009, Aug. 25, 1986.
Hoffman et al., "Activation of colonic mucosal 5-HT(4) receptors accelerates propulsive motility and inhibits visceral hypersensitivity," Gastroenterology, 142(4):844-854.e4, Epub Jan. 4, 2012.
Husebye et al., "Intestinal microflora stimulates myoelectric activity of rat small intestine by promoting cyclic initiation and aboral propagation of migrating myoelectric complex," Dig Dis Sci., 39(5):946-956, May 1994.
Ishihara et al., "Probing the role of tryptophan-derived secondary metabolism in defense responses against Bipolaris oryzae infection in rice leaves by a suicide substrate of tryptophan decarboxylase," Phytochemistry, 72(1):7-13, Epub Nov. 25, 2010, print Jan. 2011.
John et al., "Pyridoxal phosphate-dependent enzymes," Biochim Biophys Acta., 1248(2):81-96, Apr. 27, 1995.
Kashyap et al., "Complex interactions among diet, gastrointestinal transit, and gut microbiota in humanized mice," Gastroenterology, 144(5):967-977, Epub Feb. 1, 2013.
Katoh et al., "MAFFT: iterative refinement and additional methods," Methods Mol Biol., 1079:131-146, 2014.
Kim, "5-Hydroxytryptamine4 receptor agonists and colonic motility," J Smooth Muscle Res., 45(1):25-29, Feb. 2009.
Komori et al., "Structural study reveals that Ser-354 determines substrate specificity on human histidine decarboxylase," J Biol Chem., 287(34):29175-29183, Epub Jul. 5, 2012.
Manabe et al., "New-generation 5-HT4 receptor agonists: potential for treatment of gastrointestinal motility disorders," Expert Opin Investig Drugs, 19(6):765-775, Jun. 2010.
Mawe et al., "Serotonin signalling in the gut—functions, dysfunctions and therapeutic targets," Nat Rev Gastroenterol Hepatol., 10(8):473-486, Epub Jun. 25, 2013.
Metzner, "Serotonin, L-tryptophan, and tryptamine are effective inhibitors of the amino acid transport system PAT1," FASEB J., 19(11):1468-1473, Sep. 2005.
O'Hara et al., "The gut flora as a forgotten organ," EMBO Rep., 7(7):688-693, Jul. 2006.
Pettersen et al., "UCSF Chimera—a visualization system for exploratory research and analysis," J Comput Chem., 25(13):1605-1612, Oct. 2004.
Reigstad and Kashyap, "Beyond phylotyping: understanding the impact of gut microbiota on host biology," Neurogastroenterol Motil., 25(5):358-372, May 2013.
Reigstad et al., "Gut microbes promote colonic serotonin production through an effect of short-chain fatty acids on enterochromaffin cells," FASEB J., 29(4): 1395-1403, Epub Dec. 30, 2014, Print Apr. 2015.
Roager et al. "Microbial tryptophan catabolites in health and disease" Nature Communications I (2018)9:32941 DOI: 10.1038/s41467-018-05470-4 I www.nature.com/naturecommunications. (Year: 2018).
Samuel et al., "Effects of the gut microbiota on host adiposity are modulated by the short-chain fatty-acid binding G protein-coupled receptor, Gpr41," Proc Natl Acad Sci U S A., 105(43):16767-16772, Epub Oct. 17, 2008.
Schirmer et al., "Targeted covalent inactivation of protein kinases by resorcylic acid lactone polyketides," Proc Natl Acad Sci U S A., 103(11):4234-9. Epub Mar. 6, 2006.
Schneider et al., "The manifold of vitamin B6 dependent enzymes," Structure, 8(1):R1-R6, Jan. 15, 2000.
Shanahan, "The host-microbe interface within the gut," Best Pract Res Clin Gastroenterol., 16(6):915-931, Dec. 2002.
Sharma et al., "The diet and gut microflora influence the distribution of enteroendocrine cells in the rat intestine," Experientia, 52(7):664-670, Jul. 15, 1996.
Takaki et al., "Physiological responses of guinea-pig myenteric neurons secondary to the release of endogenous serotonin by tryptamine," Neuroscience, 16(1):223-240, Sep. 1985.
UniProtKB: CLOSPO_02083, Oct. 31, 2012, 1 page.
Uribe et al., "Microflora modulates endocrine cells in the gastrointestinal mucosa of the rat," Gastroenterology, 107(5): 1259-1269, Nov. 1994.
Van Poelje et al., "Pyruvoyl-dependent enzymes," Annu Rev Biochem., 59:29-59, 1990.
Weissbach et al., "Formation of indole-3-acetic acid and tryptamine in animals: a method for estimation of indole-3-acetic acid in tissues," J Biol Chem., 234(1):81-86, Jan. 1959.
Wikoff et al., "Metabolomics analysis reveals large effects of gut microflora on mammalian blood metabolites," Proc Natl Acad Sci U S A., 106(10):3698-3703, Epub Feb. 20, 2009.
Williams et al., "Discovery and characterization of gut microbiota decarboxylases that can produce the neurotransmitter tryptamine," Cell Host Microbe., 16(4):495- 503, Epub Sep. 25, 2014.
GenPept Accession: EGG84852, "hypothetical protein HMPREF9477_00579 [Lachnospiraceae bacterium 2_1_46FAA]," Jun. 10, 2013 HMPREF9477_00579, Jun. 28, 2011, 2 pages.

\* cited by examiner

FIG. 1A
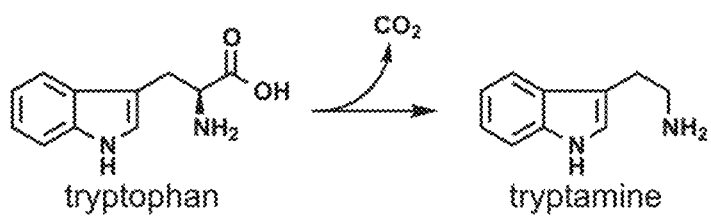
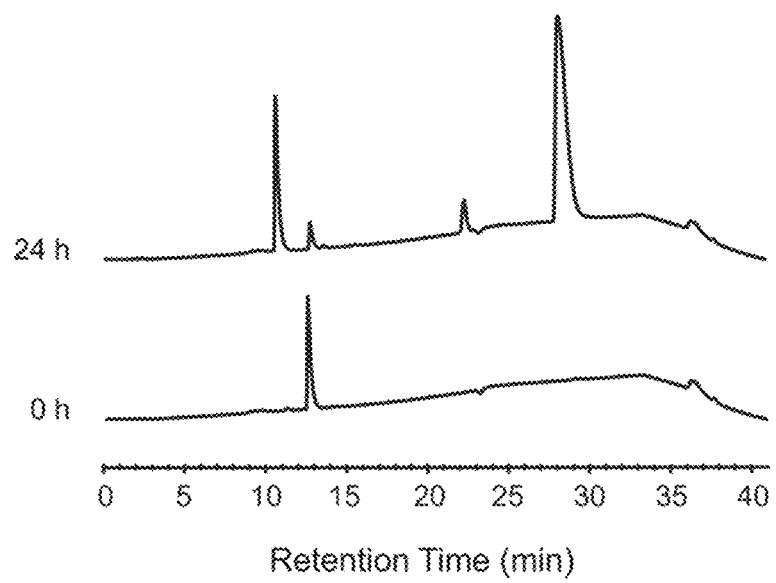
FIG. 1B

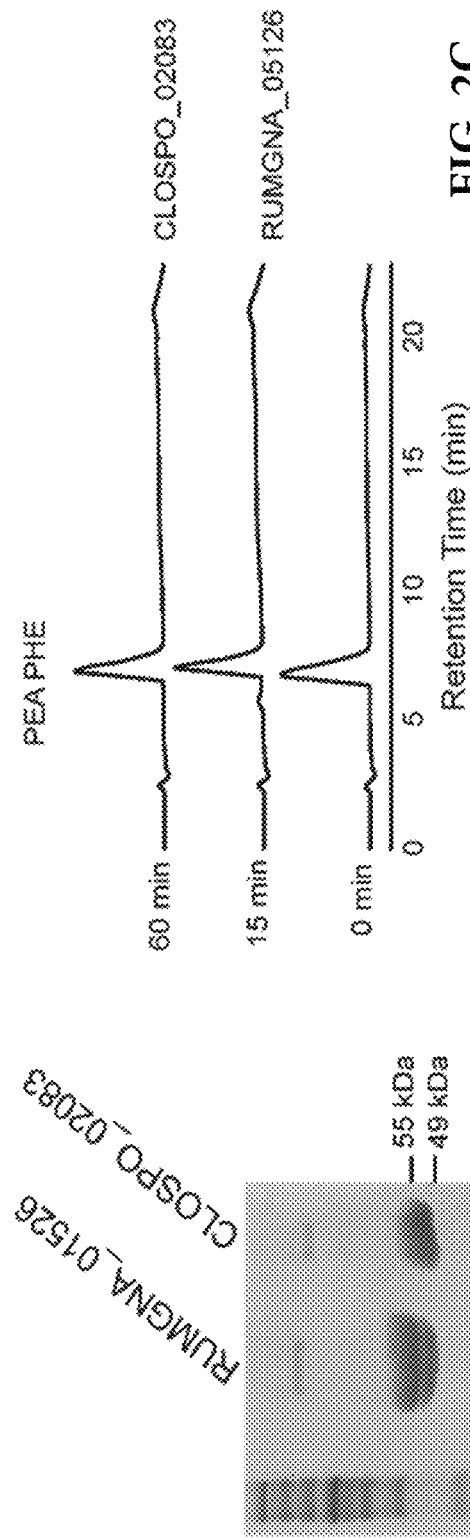
FIG. 2C
FIG. 2B
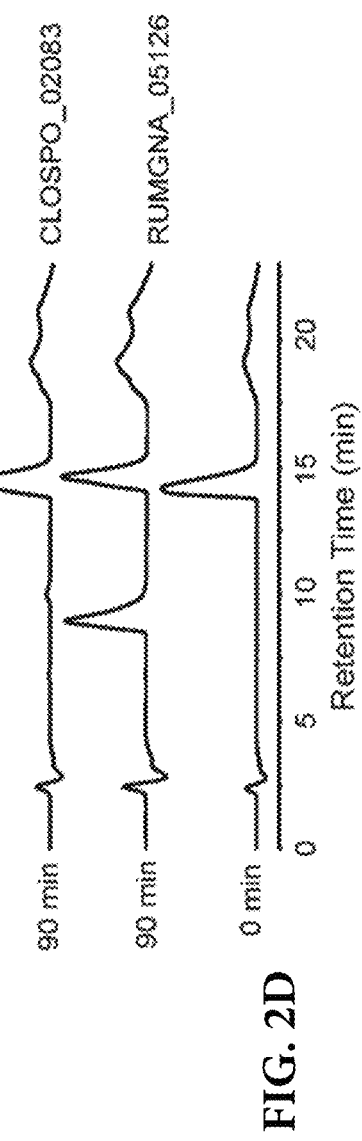
FIG. 2D

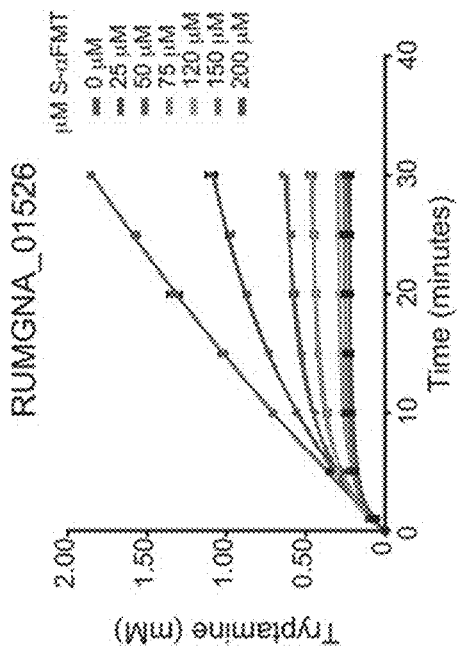
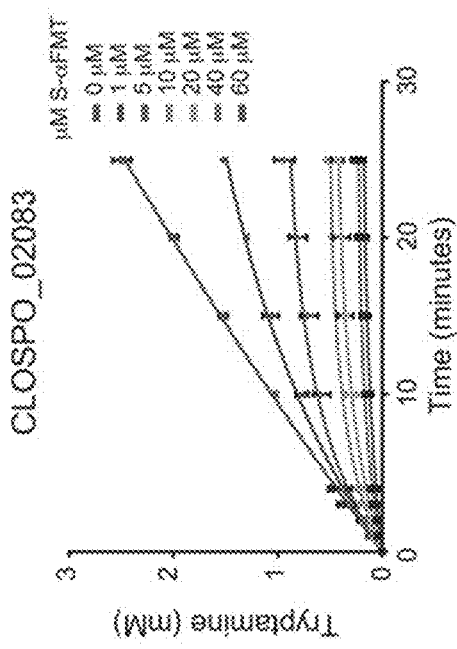
FIG. 8B
FIG. 8A
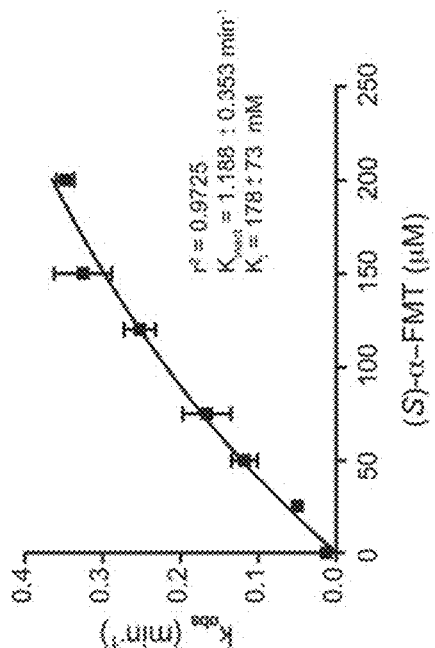
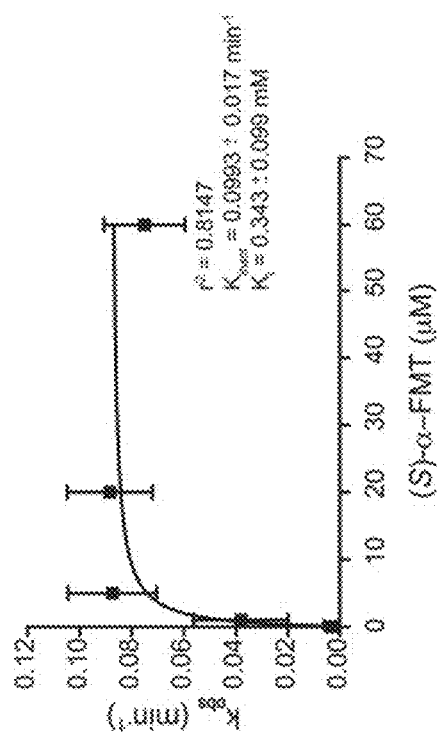
FIG. 8D
FIG. 8C

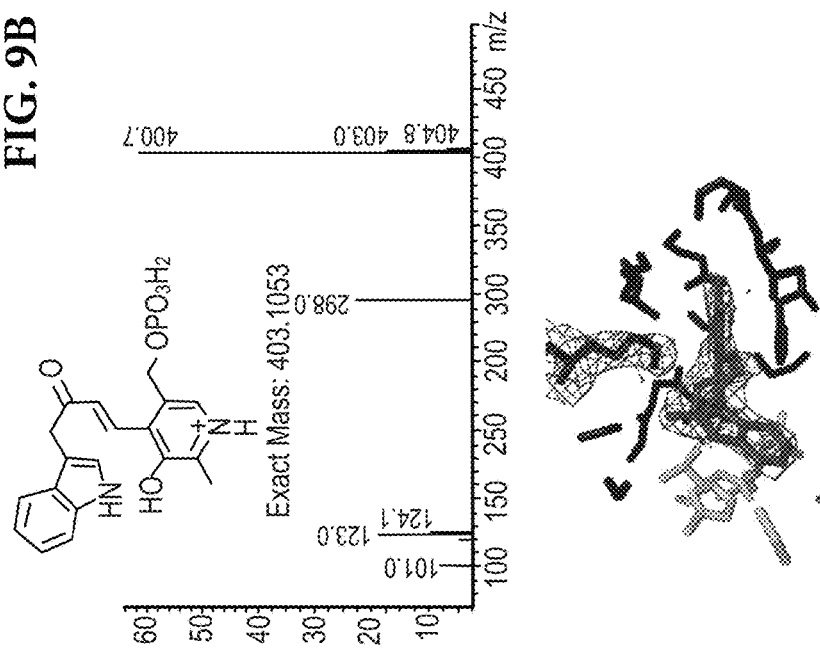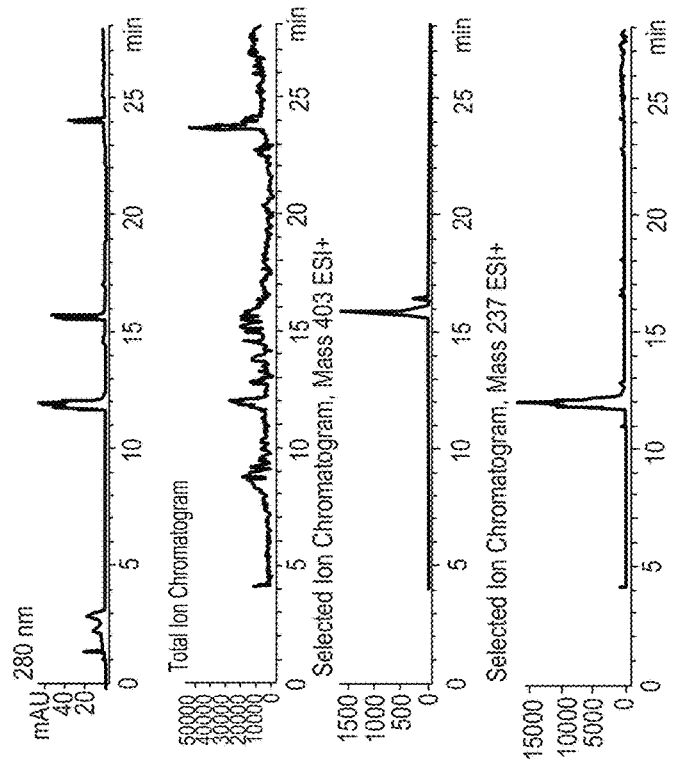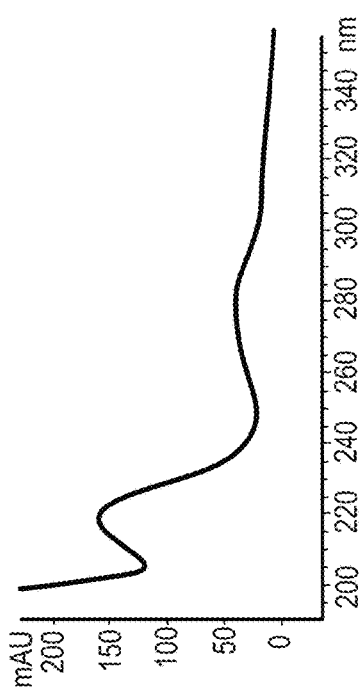
FIG. 9A  FIG. 9B  FIG. 9C  FIG. 9D

SEQUENCE LISTING

<160> NUMBER OF SEQ ID NOS: 29

<210> SEQ ID NO 1
<211> LENGTH: 28
<212> TYPE: PRT
<213> ORGANISM: Ruminococcus gnavus

<400> SEQUENCE: 1

Ser Phe Val Pro Gly Pro Ala Ile His Ala Gly Gly Ser Lys Leu Ala
1               5                   10                  15

His Lys Trp Leu Tyr Leu Lys Asp Leu Leu Thr Arg
            20                  25

<210> SEQ ID NO 2
<211> LENGTH: 28
<212> TYPE: PRT
<213> ORGANISM: Unknown
<220> FEATURE:
<223> OTHER INFORMATION: decarboxylase from a human gut microbiota

<400> SEQUENCE: 2

Ala Tyr Tyr Pro Ala Leu Thr Cys Leu Gly Phe Thr Trp Ala Ser Pro
1               5                   10                  15

Ser Lys Trp Met Tyr Leu Arg His Ala Leu Ser Arg
            20                  25

<210> SEQ ID NO 3
<211> LENGTH: 28
<212> TYPE: PRT
<213> ORGANISM: Unknown
<220> FEATURE:
<223> OTHER INFORMATION: decarboxylase from a human gut microbiota

<400> SEQUENCE: 3

Gly Tyr Phe Pro Ser Asn Gly Val Leu Gly Leu Ser Trp Gln Ser Ala
1               5                   10                  15

His Lys Trp Leu Tyr Leu Gln Ser Ala Leu Gly Arg
            20                  25

<210> SEQ ID NO 4
<211> LENGTH: 28
<212> TYPE: PRT
<213> ORGANISM: Unknown
<220> FEATURE:
<223> OTHER INFORMATION: decarboxylase from a human gut microbiota

<400> SEQUENCE: 4

Ser Phe Ile Pro Gly Pro Ala Ile His Ala Ser Asn Phe Ala Asn Ala
1               5                   10                  15

His Lys Leu Leu Tyr Leu Asp Asp Ile Leu Thr Arg
            20                  25

<210> SEQ ID NO 5
<211> LENGTH: 28
<212> TYPE: PRT
<213> ORGANISM: Unknown
<220> FEATURE:
<223> OTHER INFORMATION: decarboxylase from a human gut microbiota

<400> SEQUENCE: 5

Gly His Met Asn Ser Glu Thr Leu Met Gly Asn Asn Val Ala Tyr Glu
1               5                   10                  15

Pro His Lys Met Gly Tyr Val Phe Glu Gly Ser Lys
            20                  25

```
<210> SEQ ID NO 6
<211> LENGTH: 28
<212> TYPE: PRT
<213> ORGANISM: Unknown
<220> FEATURE:
<223> OTHER INFORMATION: decarboxylase from a human gut microbiota

<400> SEQUENCE: 6

Gly His Met Asn Ser Glu Thr Leu Met Gly Asn Asn Val Ala Tyr Glu
1               5                   10                  15

Pro His Lys Met Gly Tyr Val Tyr Asp Gly Ser Lys
            20                  25

<210> SEQ ID NO 7
<211> LENGTH: 32
<212> TYPE: PRT
<213> ORGANISM: Unknown
<220> FEATURE:
<223> OTHER INFORMATION: decarboxylase from a human gut microbiota

<400> SEQUENCE: 7

Gly His Met Asn Ala Asp Thr Leu Met Pro Asn Asn Cys Ala His Glu
1               5                   10                  15

Pro His Lys Val Gly Tyr Val Phe Glu Asp Val Asp Thr Gly Ser Lys
            20                  25                  30

<210> SEQ ID NO 8
<211> LENGTH: 32
<212> TYPE: PRT
<213> ORGANISM: Unknown
<220> FEATURE:
<223> OTHER INFORMATION: decarboxylase from a human gut microbiota

<400> SEQUENCE: 8

Gly His Met Asn Ala Asp Thr Leu Met Pro Asn Asn Cys Ala Gln Glu
1               5                   10                  15

Pro His Lys Val Gly Tyr Val Phe Glu Glu Val Ala Glu Gly Ser Lys
            20                  25                  30

<210> SEQ ID NO 9
<211> LENGTH: 5
<212> TYPE: PRT
<213> ORGANISM: Unknown
<220> FEATURE:
<223> OTHER INFORMATION: decarboxylase from a human gut microbiota

<400> SEQUENCE: 9

Gly Thr Glu Ser Pro
1               5

<210> SEQ ID NO 10
<211> LENGTH: 16
<212> TYPE: PRT
<213> ORGANISM: Unknown
<220> FEATURE:
<223> OTHER INFORMATION: decarboxylase from a human gut microbiota

<400> SEQUENCE: 10

Gln Ala Ile Gly Pro Ser Lys Glu Phe Cys Gly Arg Ser Lys Gly Ala
1               5                   10                  15

<210> SEQ ID NO 11
<211> LENGTH: 16
<212> TYPE: PRT
```

-continued

<213> ORGANISM: Unknown
<220> FEATURE:
<223> OTHER INFORMATION: decarboxylase from a human gut microbiota

<400> SEQUENCE: 11

Ile Ala Ile Ser Pro Tyr Lys Gln Trp Ser Gly Pro Ser Lys Asp Ser
1               5                   10                  15

<210> SEQ ID NO 12
<211> LENGTH: 27
<212> TYPE: PRT
<213> ORGANISM: Unknown
<220> FEATURE:
<223> OTHER INFORMATION: decarboxylase from a human gut microbiota

<400> SEQUENCE: 12

Gly Ser Met Cys Ser Asn Val Thr Asn Leu Gly Asp Pro Gly Leu Pro
1               5                   10                  15

His Lys Met Gly Tyr Leu Thr Glu Gly Thr Arg
            20                  25

<210> SEQ ID NO 13
<211> LENGTH: 32
<212> TYPE: PRT
<213> ORGANISM: Unknown
<220> FEATURE:
<223> OTHER INFORMATION: decarboxylase from a human gut microbiota

<400> SEQUENCE: 13

Lys Thr Ile Gly Ile Pro Gly Thr Lys Thr Phe Ile Gln Asn Pro Asn
1               5                   10                  15

His Ile Gly Leu Gly His Lys Met Leu Tyr Ile Glu Asn Gly Ser Arg
            20                  25                  30

<210> SEQ ID NO 14
<211> LENGTH: 27
<212> TYPE: PRT
<213> ORGANISM: Unknown
<220> FEATURE:
<223> OTHER INFORMATION: decarboxylase from a human gut microbiota

<400> SEQUENCE: 14

Ala Thr Phe Cys Thr Thr Gln Thr Asn Ala Ile Asp Lys Ser Gly His
1               5                   10                  15

Lys Tyr Gly Tyr Leu Gly Lys Thr Ala His Ile
            20                  25

<210> SEQ ID NO 15
<211> LENGTH: 27
<212> TYPE: PRT
<213> ORGANISM: Unknown
<220> FEATURE:
<223> OTHER INFORMATION: decarboxylase from a human gut microbiota

<400> SEQUENCE: 15

Ala Thr Phe Cys Gln Thr Tyr Lys Asn Ala Ile Asp Lys Ser Gly His
1               5                   10                  15

Lys Tyr Gly Tyr Leu Gly Gly Glu Ser Gln Leu
            20                  25

<210> SEQ ID NO 16
<211> LENGTH: 27
<212> TYPE: PRT
<213> ORGANISM: Unknown
<220> FEATURE:

-continued

<223> OTHER INFORMATION: decarboxylase from a human gut microbiota

<400> SEQUENCE: 16

Ala Thr Phe Val Thr Thr Tyr Ile Asn Tyr Ile Asp Glu Thr Gly His
1               5                   10                  15

Lys Phe Gly Tyr Leu Gly Ala Asn Ala Gln Ile
            20                  25

<210> SEQ ID NO 17
<211> LENGTH: 27
<212> TYPE: PRT
<213> ORGANISM: Unknown
<220> FEATURE:
<223> OTHER INFORMATION: decarboxylase from a human gut microbiota

<400> SEQUENCE: 17

Ala Thr Phe Val Thr Thr Tyr Ile Asn Tyr Ile Asp Glu Thr Gly His
1               5                   10                  15

Lys Phe Gly Tyr Leu Gly Ala Asn Ala Gln Ile
            20                  25

<210> SEQ ID NO 18
<211> LENGTH: 27
<212> TYPE: PRT
<213> ORGANISM: Unknown
<220> FEATURE:
<223> OTHER INFORMATION: decarboxylase from a human gut microbiota

<400> SEQUENCE: 18

Ala Thr Phe Val Thr Thr Tyr Ile Asn Tyr Ile Asp Glu Thr Gly His
1               5                   10                  15

Lys Phe Gly Tyr Leu Gly Ala Asn Ala Gln Ile
            20                  25

<210> SEQ ID NO 19
<211> LENGTH: 27
<212> TYPE: PRT
<213> ORGANISM: Unknown
<220> FEATURE:
<223> OTHER INFORMATION: decarboxylase from a human gut microbiota

<400> SEQUENCE: 19

Ala Thr Phe Val Ser Thr Trp Lys Asn Met Ile Asp Lys Asp Gly His
1               5                   10                  15

Lys Tyr Gly Tyr Leu Gly Gly Glu Ala Gln Val
            20                  25

<210> SEQ ID NO 20
<211> LENGTH: 27
<212> TYPE: PRT
<213> ORGANISM: Unknown
<220> FEATURE:
<223> OTHER INFORMATION: decarboxylase from a human gut microbiota

<400> SEQUENCE: 20

Ala Thr Phe Cys Gln Thr Trp Lys Asn Trp Ile Asp Lys Glu Gly His
1               5                   10                  15

Lys Phe Gly Tyr Leu Gly Gly Gln Gly Gln Val
            20                  25

<210> SEQ ID NO 21
<211> LENGTH: 26
<212> TYPE: PRT
<213> ORGANISM: Unknown

-continued

```
<220> FEATURE:
<223> OTHER INFORMATION: decarboxylase from a human gut microbiota

<400> SEQUENCE: 21

Ala Thr Phe Cys Gln Thr Trp Lys Asn Trp Ile Asp Lys Glu Gly His
1               5                   10                  15

Lys Phe Gly Tyr Leu Gly Gln Gly Gln Val
            20                  25

<210> SEQ ID NO 22
<211> LENGTH: 27
<212> TYPE: PRT
<213> ORGANISM: Unknown
<220> FEATURE:
<223> OTHER INFORMATION: decarboxylase from a human gut microbiota

<400> SEQUENCE: 22

Ala Thr Phe Cys Gln Thr Trp Lys Asn Trp Ile Asp Lys Glu Gly His
1               5                   10                  15

Lys Phe Gly Tyr Leu Gly Gly Gln Gly Gln Val
            20                  25

<210> SEQ ID NO 23
<211> LENGTH: 34
<212> TYPE: PRT
<213> ORGANISM: Artificial Sequence
<220> FEATURE:
<223> OTHER INFORMATION: consensus decarboxylase sequence
<220> FEATURE:
<221> NAME/KEY: MISC_FEATURE
<222> LOCATION: (4)..(4)
<223> OTHER INFORMATION: P, N, or G
<220> FEATURE:
<221> NAME/KEY: MISC_FEATURE
<222> LOCATION: (6)..(6)
<223> OTHER INFORMATION: P, L, N, E, D, S, T, OR Q
<220> FEATURE:
<221> NAME/KEY: MISC_FEATURE
<222> LOCATION: (8)..(8)
<223> OTHER INFORMATION: L, T, W, or Y
<220> FEATURE:
<221> NAME/KEY: MISC_FEATURE
<222> LOCATION: (12)..(12)
<223> OTHER INFORMATION: A, G, N, I, L, A, Y, M, OR W
<220> FEATURE:
<221> NAME/KEY: MISC_FEATURE
<222> LOCATION: (18)..(18)
<223> OTHER INFORMATION: K, A, Q, C, S, OR G
<220> FEATURE:
<221> NAME/KEY: MISC_FEATURE
<222> LOCATION: (29)..(29)
<223> OTHER INFORMATION: H, D, E, T, N, OR Q

<400> SEQUENCE: 23

Ala Thr Phe Xaa Cys Xaa Thr Xaa Met Ile Asn Xaa Ile Asp Lys Lys
1               5                   10                  15

Trp Xaa Glu Gly His Lys Phe Gly Tyr Leu Gly Gly Xaa Val Ala Gly
            20                  25                  30

Gln Arg

<210> SEQ ID NO 24
<211> LENGTH: 28
<212> TYPE: PRT
<213> ORGANISM: Unknown
<220> FEATURE:
<223> OTHER INFORMATION: tryptophan decarboxylase from a Lachnospiraceae
      bacterium

<400> SEQUENCE: 24
```

```
Gly Phe Val Pro Gly Pro Ala Ile His Ala Gly Gly Ser Lys Leu Ala
1               5                   10                  15

His Lys Trp Leu Tyr Leu Lys Asp Val Leu Thr Arg
            20                  25
```

<210> SEQ ID NO 25
<211> LENGTH: 28
<212> TYPE: PRT
<213> ORGANISM: Blautia hansenii

<400> SEQUENCE: 25

```
Gly Phe Val Pro Gly Pro Ala Ile His Ala Gly Gly Ser Lys Leu Ala
1               5                   10                  15

His Lys Trp Leu Tyr Leu Lys Asp Val Leu Thr Arg
            20                  25
```

<210> SEQ ID NO 26
<211> LENGTH: 28
<212> TYPE: PRT
<213> ORGANISM: Clostridium nexile

<400> SEQUENCE: 26

```
Gly Phe Val Pro Gly Pro Ala Ile His Ala Gly Gly Ser Lys Leu Ala
1               5                   10                  15

His Lys Trp Leu Tyr Leu Lys Asp Ile Leu Thr Arg
            20                  25
```

<210> SEQ ID NO 27
<211> LENGTH: 28
<212> TYPE: PRT
<213> ORGANISM: Desulfitobacterium dehalogenans

<400> SEQUENCE: 27

```
Gly Phe Ile Pro Gly Pro Ala Arg His Ala Gly Ser Trp Val Ser Ala
1               5                   10                  15

His Lys Trp Leu Tyr Leu Lys Asp Leu Leu Thr Arg
            20                  25
```

<210> SEQ ID NO 28
<211> LENGTH: 28
<212> TYPE: PRT
<213> ORGANISM: Clostridium asparagiforme

<400> SEQUENCE: 28

```
Ala Cys Ile Pro Ser Pro Val Pro His Ala Gly Cys Val Met Asn Ala
1               5                   10                  15

His Lys Trp Leu Tyr Leu Thr Asp Ala Leu Thr Arg
            20                  25
```

<210> SEQ ID NO 29
<211> LENGTH: 28
<212> TYPE: PRT
<213> ORGANISM: Artificial Sequence
<220> FEATURE:
<223> OTHER INFORMATION: consensus trp decarboxylase sequence
<220> FEATURE:
<221> NAME/KEY: MISC_FEATURE
<222> LOCATION: (25)..(25)
<223> OTHER INFORMATION: L, V, I, or A

<400> SEQUENCE: 29

```
Gly Phe Val Pro Gly Pro Ala Ile His Ala Gly Gly Ser Lys Leu Ala
1               5                   10                  15

His Lys Trp Leu Tyr Leu Lys Asp Xaa Leu Thr Arg
            20                  25
```

US 11,878,002 B2

METHODS AND MATERIALS FOR USING *RUMINOCOCCUS GNAVUS* OR *CLOSTRIDIUM SPOROGENES* TO TREAT GASTROINTESTINAL DISORDERS

CROSS-REFERENCE TO RELATED APPLICATIONS

This application is a continuation of U.S. application Ser. No. 16/388,405, filed on Apr. 18, 2019, which is a continuation of U.S. application Ser. No. 15/235,782, filed on Aug. 12, 2016, which claims the benefit of U.S. Provisional Application Ser. No. 62/204,270, filed on Aug. 12, 2015, the contents of each of which are herein incorporated by reference in their entirety.

FEDERAL FUNDING

This invention was made with government support under DK100638 and DK114007 awarded by the National Institutes of Health. The government has certain rights in the invention.

SEQUENCE LISTING

The document includes a sequence listing in electronic format submitted to the United States Patent and Trademark Office via the electronic filing system. The ASCII text file, which is incorporated-by-reference herein, is titled "NVM-005C2 ST25.txt," was created on Apr. 5, 2021, and has a size of 11,026 bytes.

BACKGROUND

1. Technical Field

This document relates to bacterial compositions. For example, this document provides bacterial compositions containing at least one bacterial strain having tryptophan decarboxylase activity and methods for using bacterial compositions to improve gastrointestinal epithelial function or to treat gastrointestinal disorders.

2. Background Information

Consuming particular microorganisms in the form of a probiotic formulation can provide health benefits to mammals. There are hundreds of different bacterial strains within a human's digestive system. It is believed that some of these different bacteria help maintain a healthy digestive tract and help digest food.

Serotonin (5-hydroxy tryptamine; 5HT) and its receptors (5HT3R and 5HT4R) play an important role in gastrointestinal motility, secretion, and sensation, processes that are often disrupted in functional gastrointestinal disorders. 5HTR4 agonists can be used to treat symptoms of irritable bowel syndrome. Unfortunately, 5HTR4 agonists exhibit systemic cardiac side effects, and have largely been withdrawn from the market.

SUMMARY

This document provides materials and methods related to bacterial compositions containing at least one bacterial strain having tryptophan decarboxylase activity. For example, this document provides bacterial compositions containing at least one bacterial strain having tryptophan decarboxylase activity in the form of an oral medicament or dietary supplement (e.g., a pill, tablet, or capsule). In addition, this document provides methods for using a bacterial composition containing at least one bacterial strain having tryptophan decarboxylase activity to treat a gastrointestinal disorder.

As described herein, bacteria endogenously having tryptophan decarboxylase activity (e.g., *Ruminococcus gnavus* and/or *Clostridium sporogenes*) and/or bacteria designed to express an exogenous nucleic acid encoding a polypeptide having tryptophan decarboxylase activity can be administered to a mammal (e.g., a human) having a gastrointestinal disorder (e.g., reduced gastrointestinal motility) under conditions wherein tryptophan present in the gastrointestinal tract is converted to tryptamine or other compounds that have the ability to improve gastrointestinal functions (e.g., gastrointestinal motility, gastrointestinal secretion, and sensation).

In general, one aspect of this document features a method for treating a gastrointestinal disorder in a mammal. The method comprises, or consists essentially of, administering a composition comprising, or consisting essentially of, at least one live bacterial organism having tryptophan decarboxylase activity to the mammal under conditions wherein gastrointestinal function of the mammal is improved. The mammal can be a human. The gastrointestinal disorder can be irritable bowel syndrome. The at least one bacterial organism can comprise endogenous tryptophan decarboxylase activity. The at least one bacterial organism can have endogenous tryptophan decarboxylase activity is *Ruminococcus gnavus* or *Clostridium sporogenes*. The at least one bacterial organism can have exogenous tryptophan decarboxylase activity. The at least one bacterial organism can have exogenous tryptophan decarboxylase activity is *Escherichia coli* or *Bacteroides thetaiotaomicron*. The composition can be a pill, tablet, or capsule. The composition can be a pill, tablet, or capsule configured to deliver the at least one bacterial organism to the intestines of the mammal. The composition can comprise no more than one bacterial species, and wherein the bacterial organism is a member of the one bacterial species. The bacterial species can be *Ruminococcus gnavus* or *Clostridium sporogenes*. The method can comprise identifying the mammal as having the gastrointestinal disorder prior to the administration.

In another aspect, this document features a composition comprising, or consisting essentially of, at least one bacterial organism comprising exogenous tryptophan decarboxylase activity. The at least one bacterial organism can be *Escherichia coli* or *Bacteroides thetaiotaomicron*. The composition can be a pill, tablet, or capsule. The composition can comprise no more than one bacterial species, and wherein the bacterial organism is a member of the one bacterial species. The composition can comprise tryptophan.

In another aspect, this document features a composition comprising tryptophan and at least one bacterial organism comprising tryptophan decarboxylase activity.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-1B show tryptamine production by C. sporogenes. (A) The proteinogenic amino acid L-tryptophan is decarboxylated to tryptamine, a biogenic amine neurotransmitter, by the action of pyridoxal phosphate (PLP)-dependent decarboxylases. (B) Whole C. sporogenes were grown anaerobically in minimal media containing 5 g/L tryptophan and clarified supernatant was analyzed by HPLC. C. sporogenes converts tryptophan (12.5 minutes) into tryptamine (TAM, 10.5 minutes), indole lactic acid (ILA, 22 minutes), and indole propionic acid (IPA, 28 minutes).

FIGS. 2A-2D show characterization of tryptamine production. (A) NMR of C. sporogenes produced tryptamine compared to standard (Sigma-Aldrich). Standard tryptamine is shown in the top spectrum, and C. sporogenes-produced tryptamine is shown in the bottom spectrum. (B) SDS-PAGE of purified CLOSPO_02083 and RUMGNA_01526. Using a BioRad ReadyGel, Precast SDSPAGE 10% Tris-HCl, 1 µL of purified protein was loaded. Lane 1: Precision Plus Protein Prestained Standards, Dual Color, Lane 2: RUGMNA_01526 55 kDa, and Lane 3: CLOSPO_02083 49 kDa. (C, D) Biochemical activity of CLOSPO_02083 and RUMGNA_01526 with phenylalanine and tyrosine substrates. HPLC traces for (C) phenylalanine or (D) tyrosine decarboxylation by CLOSPO_02083 or RUMGNA_01526.

FIGS. 8A-8D show decarboxylase inhibition by (S)-α-FMT. (A) Progress curve of tryptamine production by CLOSPO_02083 in the presence of 10 mM tryptophan at various concentrations of inhibitor. (B) Progress curve of tryptamine production by RUMGNA_01526 in the presence of 2.5 mM tryptophan at various concentrations of inhibitor. Data were fit to an equation to obtain $k_{obs}$. (C and D) Plot of $k_{obs}$ versus [I]. CLOPSO_02083 was inhibited more potently by (S)-α-FMT than RUMGNA_01526 due to a higher binding affinity of the inhibitor. Error represented standard error of the mean.

FIGS. 9A-9D show a structure determination of (S)-α-FMT-PLP adduct. (A) 280 nm UV trace, total ion chromatogram, and selected ion chromatograms for the released adduct. (B) Mass spectrum of adduct shows a compound with a mass of 403, corresponding to the structure shown in the inset. (C) UV-Vis spectrum of adduct. (D) Electron density shows separation of adduct and lysine residue.

DETAILED DESCRIPTION

Figure 2A:
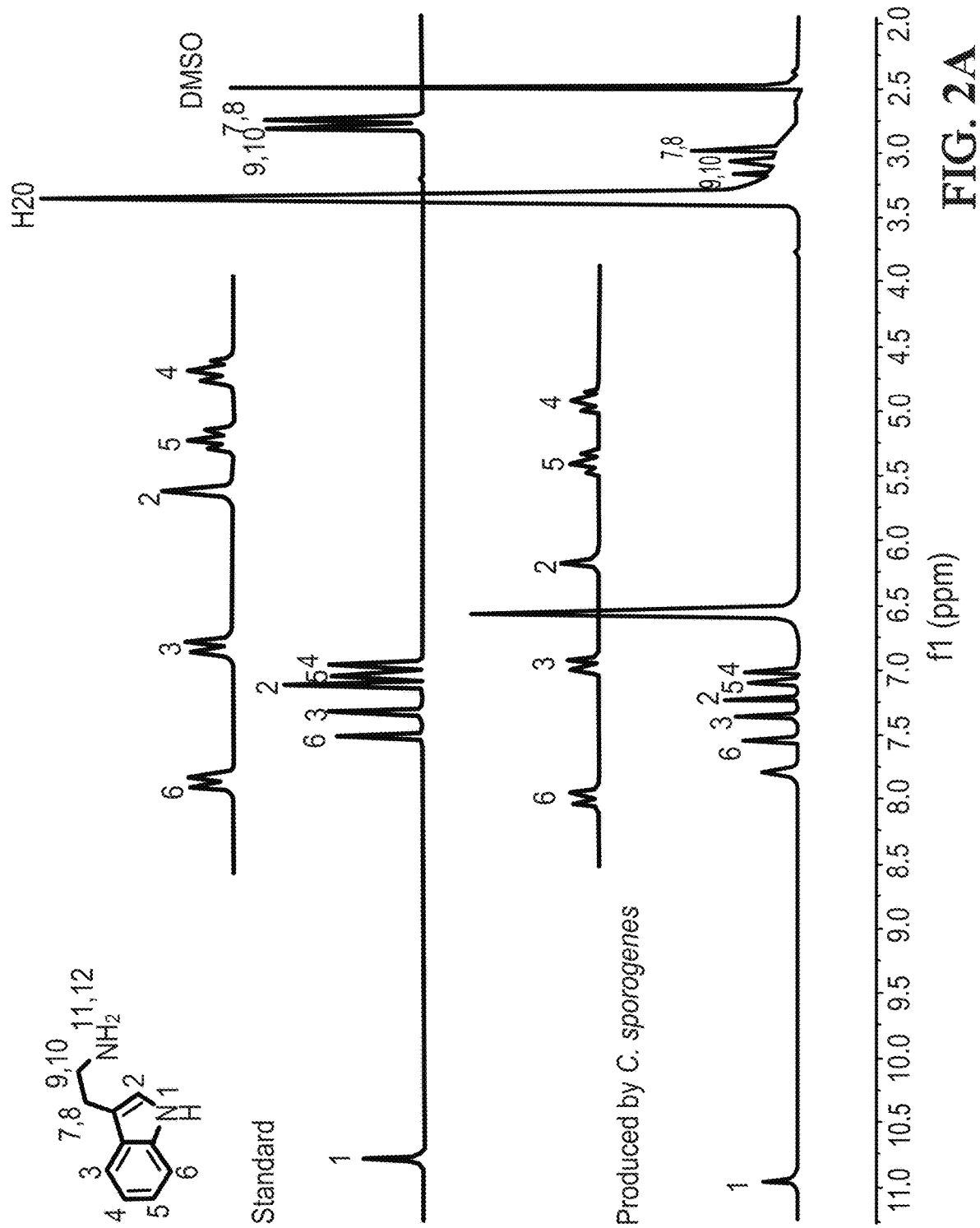

This document provides materials and methods related to bacterial compositions containing at least one bacterial strain having tryptophan decarboxylase activity. In addition, this document provides methods for using a bacterial composition containing at least one bacterial strain having tryptophan decarboxylase activity to improve gastrointestinal epithelial function and/or to treat gastrointestinal disorders (e.g., functional gastrointestinal disorders such as irritable bowel syndrome). For example, this document provides bacterial compositions containing at least one bacterial strain having tryptophan (trp) decarboxylase activity.

A bacterial composition provided herein can include at least one type of bacteria (e.g., intestinal bacteria) having trp decarboxylase activity. An "intestinal bacteria" is any bacterial species that normally lives in the digestive tracts of a mammal. Examples of intestinal bacteria that can be used as described herein include, without limitation, those belonging to the genera *Prevotella*, *Bacteroides*, *Clostridium*, *Faecalibacterium*, *Eubacterium*, *Ruminococcus*, *Peptococcus*, *Peptostreptococcus*, *Bifidobacterium*, *Escherichia*, *Lactobacillus*, *Akkermansia*, and *Roseburia*. In some cases, a fungal composition containing a fungal organism (e.g., intestinal fungus) having tryptophan decarboxylase activity can be used as described herein in place of a bacterial composition provided herein or in addition to a bacterial composition provided herein. Examples of intestinal fungi that can be used as described herein include, without limitation, *Candida*, *Saccharomyces*, *Aspergillus*, and *Penicillium*.

A composition containing at least one bacterial strain having trp decarboxylase activity can contain one or more additional probiotic microorganisms. Examples of other probiotic microorganisms that can be included within a composition containing at least one bacterial strain having trp decarboxylase activity include, without limitation, *Prevotella coprii*, *Bifidobacterium infantis*, *Lactobacillus rhamnosis* GG *Lactobacillus plantarum*, *Bifidobacterium breve*, *Bifidobacterium longum*, *Lactobacillus acidophilus*, *Lactobacillus paracasei*, *Lactobacillus bulgaricus*, *Streptococcus thermophilus*, and *Faecalibacterium prauznitzii*. Trp decarboxylase activity is the enzymatic ability to convert tryptophan to tryptamine. In some cases, the bacteria having trp carboxylase activity may have native (endogenous) trp decarboxylase activity. Examples of bacteria containing endogenous trp decarboxylase activity include, without limitation, *Ruminococcus gnavus* and *Clostridium sporogenes*. In some cases, bacteria lacking trp decarboxylase activity may be engineered to have trp decarboxylase activity. For example, bacteria can be engineered to express an exogenous nucleic acid encoding a polypeptide having tryptophan decarboxylase activity. Bacteria engineered to have trp decarboxylase activity can include an exogenous nucleic acid encoding a polypeptide having tryptophan decarboxylase activity derived from any appropriate source. Examples of bacteria that can be engineered to express a polypeptide having tryptophan decarboxylase activity include, without limitation, *Escherichia coli* and *Bacteroides thetaiotaomicron*. Examples of nucleotide sequences that encode a trp decarboxylase include, without limitation, those nucleic acid sequence that encode the amino acid sequence set forth in GenBank® Accession No. ZP_02040762 (GI No. 154503702). Any appropriate method can be used to engineer bacteria to express an exogenous nucleic acid encoding a polypeptide having trp decarboxylase activity. In some cases, a promoter sequence can be operably linked to a nucleic acid sequence that encodes a polypeptide having tryptophan decarboxylase activity to drive expression of the tryptophan decarboxylase. An example of such a promoter sequence includes, without limitation, a CMV promoter. In some cases, a bacterial strain having trp decarboxylase activity can be engineered to have enhanced tryptophan production.

Compositions provided herein can include any amount of bacteria having tryptophan decarboxylase activity. In some cases, a composition provided herein can contain bacteria having tryptophan decarboxylase activity (e.g., *R. gnavus* and/or *C. sporogenes*) in an amount such that from about 0.001 to about 100 percent (e.g., from about 1 percent to about 95 percent, from about 10 to about 95 percent, from about 25 to about 95 percent, from about 50 to about 95 percent, from about 20 to about 80 percent, from about 50 to about 95 percent, from about 60 to about 95 percent, from about 70 to about 95 percent, from about 80 to about 95 percent, from about 90 to about 95 percent, from about 95 to about 99 percent, from about 50 to about 100 percent, from about 60 to about 100 percent, from about 70 to about 100 percent, from about 80 to about 100 percent, from about 90 to about 100 percent, or from about 95 to about 100 percent), by weight, of the composition can be bacteria having tryptophan decarboxylase activity. In some cases, a composition provided herein can contain from about $10^3$ to about $10^8$ bacteria having tryptophan decarboxylase activity.

In some cases, a composition provided herein can contain bacteria having tryptophan decarboxylase activity (e.g., *R. gnavus* and/or *C. sporogenes*) in the amounts and dosages as described elsewhere for probiotic bacteria (U.S. Patent Application Publication No. 2008/0241226; see, e.g., paragraphs [0049-0103]). In addition, a composition provided herein containing bacteria having tryptophan decarboxylase activity (e.g., *R. gnavus* and/or *C. sporogenes*) can be administered as described elsewhere for probiotic bacteria (U.S. Patent Application Publication No. 2008/0241226; see, e.g., paragraphs [0049-0103]).

Bacteria having tryptophan decarboxylase activity can be obtained from the digestive system of any appropriate mammal (e.g., a human). For example, *R. gnavus* and/or *C. sporogenes* can be isolated from small intestinal mucosa (e.g., a small bowel biopsy or aspirate sample) of a human (e.g., a human patient diagnosed with celiac disease). *R. gnavus* and/or *C. sporogenes* strains can be identified via 16S rRNA PCR using 16S rRNA primers. In some cases, bacteria having tryptophan decarboxylase activity can be obtained from the American Type Culture Collection (e.g., *C. sporogenes* ATCC 15579 and *R. gnavus* ATCC 29149).

Any appropriate method can be used to obtain a culture of bacteria having tryptophan decarboxylase activity. For example, microbial culturing techniques can be used to obtain bacteria having trp decarboxylase activity. In general, bacteria having tryptophan decarboxylase activity can be cultured in broth containing milk (e.g., skim milk) to obtain a culture containing greater than $1 \times 10^8$ bacteria per mL of broth. The bacteria can be removed from the broth via centrifugation. Once obtained, the bacteria having tryptophan decarboxylase activity can be formulated into a medicament or nutritional supplement composition for administration to a mammal (e.g., a human), can be added to a food product for consumption, or can be frozen for later use.

In some cases, a preparation of bacteria having tryptophan decarboxylase activity, which can be stored frozen in 2X skim milk, can be thawed and grown on CDC Anaerobe Laked Sheep Blood Agar with kanamycin and vancomycin (KV) (Becton, Dickson and Company, Sparks, MD, product number 221846) in an anaerobe jar with AnaeroPack System (product number 10-01, Mitsubishi Gas Chemical America, Inc., New York, NY). The culture can be incubated at 35-37° C. for at least 48 hours.

A composition containing at least one bacterial strain having trp decarboxylase activity can be in the form of an oral medicament or nutritional supplement. For example, compositions containing at least one bacterial strain having trp decarboxylase activity can be in the form of a pill, tablet, powder, liquid, or capsule. Tablets or capsules can be prepared with pharmaceutically acceptable excipients such as binding agents, fillers, lubricants, disintegrants, or wetting agents. In some cases, the tablets can be coated. In some cases, a composition containing at least one bacterial strain having trp decarboxylase activity can be formulated such that bacteria having trp decarboxylase activity are encapsulated for release within the intestines of a mammal. Liquid preparations for oral administration can take the form of, for example, solutions, syrups, or suspension, or they can be presented as a dry product for constitution with saline or other suitable liquid vehicle before use. In some cases, a composition provided herein containing at least one bacterial strain having trp decarboxylase activity (e.g., *R. gnavus* and/or *C. sporogenes*) can be in a dosage form as described elsewhere (U.S. Patent Application Publication No. 2008/0241226; see, e.g., paragraphs [0129-0135]). For example, a composition provided herein can be in the form of a food product formulated to contain at least one bacterial strain having trp decarboxylase activity (e.g., *R. gnavus* and/or *C. sporogenes*). Examples of such food products include, without limitation, milk (e.g., acidified milk), yogurt, milk powder, tea, juice, beverages, candies, chocolates, chewable bars, cookies, wafers, crackers, cereals, treats, and combinations thereof.

A composition containing at least one bacterial strain having trp decarboxylase activity can contain other ingredients such as tryptophan, buffers, radical scavengers, antioxidants, reducing agents, or mixtures thereof. For example, a composition containing at least one bacterial strain having trp decarboxylase activity can be formulated together with one or more additional ingredients (e.g., tryptophan) to form a single composition. In some cases, ingredients such as tryptophan can be provided to a mammal in a separate composition. For example, a mammal can be administered in two compositions; one containing at least one bacterial strain having trp decarboxylase activity, and one containing tryptophan. Examples of other additional ingredients that can be formulated into a single composition or a separate composition for delivery to a mammal (e.g., a human) include, without limitation, those ingredients described elsewhere (U.S. Patent Application Publication No. 2008/0241226; see, e.g., paragraphs [0104-0128]).

In some cases, a composition containing at least one bacterial strain having trp decarboxylase activity can contain a pharmaceutically acceptable carrier for administration to a mammal, including, without limitation, sterile aqueous or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Pharmaceutically acceptable carriers also can include physiologically acceptable aqueous vehicles (e.g., physiological saline) or other known carriers for oral administration.

This document also provides methods and materials for using a composition containing at least one bacterial strain having trp decarboxylase activity to treat a mammal having a gastrointestinal (GI) disorder. Examples of mammals that can be treated as described herein include, without limitation, humans, monkeys, dogs, cats, cows, horses, pigs, and sheep. In some cases, a composition provided herein can be used to treat a functional GI disorder. Functional GI disorders are GI disorders in which the bowel looks normal, but has abnormal function (pathophysiology) such as altered gut motility, secretion, and sensation. Examples of GI disorders include, without limitation, functional gastrointestinal disorders (e.g., functional constipation), irritable bowel syndrome (IBS), and inflammatory bowel diseases (e.g., infectious colitis, ulcerative colitis, Crohn's disease, ischemic colitis, radiation colitis, and microscopic colitis). In some cases, a composition containing at least one bacterial strain having trp decarboxylase activity can be used as a nutritional supplement to supplement a mammal's diet with bacterial organisms having the ability to improve gastrointestinal functions. Examples of gastrointestinal functions include, without limitation, gastrointestinal motility, gastrointestinal secretion, and sensation.

Any amount of a composition containing at least one bacterial strain having trp decarboxylase activity can be administered to a mammal. The dosages of the compositions provided herein can depend on many factors including the desired results. Typically, the amount of bacteria having trp decarboxylase activity contained within a single dose can be an amount that effectively exhibits improved gastrointestinal function within the mammal. For example, a composition containing at least one bacterial strain having trp decarboxylase activity can be formulated in a dose such that a mammal receives from about 10' to about 109 bacteria having trp decarboxylase activity.

The final pH of a composition containing at least one bacterial strain having trp decarboxylase activity can be from about 3.5 to about 9.5 (e.g., from about 4.0 to about 9.0; from about 4.5 to about 9.0; from about 4.5 to about 8.5; from about 5.0 to about 8.5; or from about 6.5 to about 8.0). To obtain such a pH, the pH of the composition can be adjusted using a pH-adjusting agent, for example. It will be appreciated that pH adjustment can be accomplished with any of a wide variety of acids should the composition have a pH that is too high (e.g., greater than 10.0 before adjustment). Likewise, pH adjustment can be accomplished with any of a wide variety of bases should the composition have a pH that is too low (e.g., less than 3.0 before adjustment).

The invention will be further described in the following examples, which do not limit the scope of the invention described in the claims.

EXAMPLES

Example 1: Characterization of Gut Microbiota Decarboxylases that can Produce the Neurotransmitter Tryptamine

*Clostridium sporogenes* was found to be capable of decarboxylating tryptophan (trp) to tryptamine (FIG. 1A). Trp decarboxylase enzymes from *C. sporogenes*, *Ruminococcus gnavus*, along with additional decarboxylases identified via phylogeny-informed screen were characterized. In addition, structural determinants of Trp selectivity in the *R. gnavus* decarboxylase were explored, and it was found that at least 10% of the human population harbors one of these enzymes.

Bacterial Growth Conditions

*Clostridium sporogenes* ATCC 15579 was grown in reinforced *clostridium* medium (BD) supplemented with MEM Vitamins (GIBCO) and incubated anaerobically at 37° C. *Ruminococcus gnavus* ATCC 29149 was grown in brain heart infusion medium (BD) supplemented with yeast extract (5 g/L) and hemin (5 g/L) and incubated anaerobically at 37° C. For the qualitative cell-based decarboxylation assay, cultures were grown to stationary phase in rich medium, and the cell mass was transferred to a minimal medium (Bell, 1976 *Med. J. Aust.* 2:481-484) containing 5 g/L tryptophan, tyrosine, or phenylalanine. Cultures were incubated at 37° C. for 24-72 hours before analysis of the culture fluid by HPLC.

Expression and Purification of CLOSPO_02083 and RUMGNA_01526

Expression constructs were transformed into *E. coli* BL21 (DE3) cells, grown to saturation in LB medium (Fisher Scientific) supplemented with kanamycin (50 mg/mL) at 37° C., and diluted 1:33 into the same medium. The expression of RUMGNA_01526 N-terminal His6 fusion proteins was induced at $OD_{600}$ 0.6 with 1 mM isopropyl 3-D-thiogalactopyranoside, and overexpression was allowed to proceed at 25° C. for 16-20 hours. Cells from 1 L of culture were pelleted by centrifugation (10 min at 5200×g), resuspended in 40 mL of buffer A (300 mM NaCl, 50 mM $NaH_2PO_4$, 10 mM Imidazole, pH 8.0), and lysed by passage through a cell disruptor (EmulsiFlex C3, Avestin, Ottawa) at 10,000 pounds per square inch. Cell debris was removed by centrifugation (20 minutes at 31,000×g), and the supernatant was incubated with 1.5 mL of Ni-nitrilotriacetic acid resin (QIAGEN, Valencia, CA) at 4° C. for 1 hour. After the unbound fraction was discarded, the resin was resuspended in 30 mL of buffer B (300 mM NaCl, 50 mM $NaH_2PO_4$, 20 mM Imidazole, pH 8.0), loaded onto a column, and washed with 60 mL of buffer B. Recombinant enzyme was eluted from the column with buffer C (300 mM NaCl, 50 mM $NaH_2PO_4$, 250 mM Imidazole, pH 8.0) and dialyzed at 4° C. against 4 L of buffer D (50 mM Tris-HCL pH 7.5, 300 mM NaCl). The protein was used immediately, and a fresh batch was purified for each enzymatic assay. The concentrations of purified enzyme were determined spectrophotometrically using a Coomassie Protein Assay (Thermo Fisher). The expression of CLOSPO_02083 N-terminal His6 fusion proteins was performed as described except for the following: LB medium was supplemented with 10 mM tryptophan and 30 mM PLP, cultures were expressed for 16-20 hours at 20° C., buffers A and D contained 30 mM PLP, and 1.0 mL of Ni-nitrilotriacetic acid resin was used.

Qualitative Cell-Based Assay for Decarboxylase Substrate Selectivity

Overnight cultures of *E. coli* BL21 (DE3) expressing pET-28a-decarboxylase constructs were diluted (1:20) into fresh LB medium containing 50 mg/mL kanamycin and grown for 90 minutes at 37° C. Cells were pelleted by centrifugation and resuspended in M9 minimal medium containing 5 mg/mL of tryptophan, tyrosine, or phenylalanine and 1 mM isopropyl β-D-thiogalactopyranoside. After 24 hours, 100 mL of clarified supernatant was analyzed by HPLC.

Cloning Candidate Decarboxylase Genes

Candidate decarboxylase genes were cloned from genomic DNA prepared from each strain using Phusion High Fidelity DNA Polymerase (NEB). PCR products were purified (MinElute, Qiagen) and used directly as primers in a CPEC reaction with pET-28a (Novagen) that were previously digested with NdeI and XhoI (98° C. for 30 seconds; 6 cycles of 98° C. for 10 seconds, 55° C. for 30 seconds, 72° C. for 3 minutes; 72° C. for 5 minutes). The identities of the resulting pET-28a-decarboxylase constructs were confirmed by DNA sequencing.

HPLC Analysis of Culture Fluid from *E. coli* Expressing Putative Decarboxylases Samples of cell-free supernatant containing tryptophan, phenylalanine, or tyrosine were analyzed on an Agilent 1200 series HPLC equipped with a diode array detector using a ThermoScientificHypercarb column (100 mm×4.6 mm×5 m) at a flow rate of 1.0 mL/minute at ambient temperature. There were four mobile phase solvents: (A) water, (B) acetonitrile, (C) isopropanol, and (D) methanol, each supplemented with 0.1% TFA (trifluoroacetic acid). The elution gradient had the following profile: 5.0-30.8% B, 5.0-30.8% C, and 2.0% D from 0-14 minutes; 30.8-49.0% B, 30.8-49.0% C, 2.0% D from 14-17 minutes; and 49.0-5.0% B, 49.0-5.0% C, 2.0% D from 17-20 minutes; 5.0% B, 5.0% C, 2.0% D from 20-23 minutes. Standard elution times were as follows: tryptophan 13.0 minutes (monitored at 280 nm), tryptamine 11.0 minutes (280 nm); phenylalanine 6.9 minutes (220 nm), phenethylamine 5.6 minutes (220 nm), tyrosine 6.8 minutes (220 nm), tyramine 5.1 minutes (220 nm).

Kinetic Characterization of CLOSPO_02083 and RUMGNA 01526 Activity with Aromatic Amino Acid Substrates Reaction mixtures contained 50 mM sodium phosphate pH 6.5, 300 mM NaCl, and 40 mM PLP. Reactions were initiated by the addition of enzyme and terminated by quenching aliquots with 1 volume of MeOH and performed at 37° C. All substrates purchased from Sigma-Aldrich.

To determine the kinetic parameters for the decarboxylation of tryptophan by RUMGNA_01526, RUMGNA_01526 was added to a final concentration of 10 nM, and $k_{cat}$ and $K_m$ were determined by varying the concentration of tryptophan from 0.15-10 mM. Reactions proceeded for 7 minutes and were quenched as described. 100 µL of the quenched reaction was analyzed by HPLC. Peak areas were integrated and compared with a standard curve to calculate product concentration. Triplicate measurements were made from a single batch of purified enzyme. Initial velocity data were fit to the Michaelis-Menten equation by using the program GraphPad. The allosteric sigmoidal model was used by fitting to the Hill equation: $y=v_{max}*x^h/(K_{0.5}^h+x^h)$, where h is the Hill coefficient and $K_{0.5}$ is the apparent concentration at half maximal velocity.

Under the same buffer and reaction conditions, the kinetic parameters for the decarboxylation of phenylalanine by RUMGNA_01526 were determined by adding RUMGNA_01526 to a final concentration of 500 nM, and the concentration of phenylalanine varied from 5-80 mM. Reactions proceeded for 10 minutes. The kinetic parameters for the decarboxylation of tryptophan by CLOSPO_02083 were determined by adding CLOSPO_02083 to a final concentration of 100 nM, and the concentration of tryptophan varied from 0.15-24.5 mM. Reactions proceeded for 6 minutes. Decarboxylation of phenylalanine by CLOSPO_02083 was not observed under saturation conditions using 1 µM enzyme and 90 mM substrate for 60 minutes. Decarboxylation of tyrosine by RUMGNA_01526 and CLOSPO_02083 was observed using 1 µM enzyme with 2.28 mM tyrosine for 90 minutes.

Experiments with the inhibitor (S)-α-FMT were performed by analyzing product formation over time after the addition of (S)-α-FMT to pre-incubated enzyme and substrate at a concentration of $3*K_m$ (2.5 mM Trp for RUMGNA_01526, and 10 mM Trp for CLOSPO_02083). Progress curves were fitted to the equation $[P]=(v_i/k_{obs})(1-\exp(-k_{Obs}t))$, where P is the product formed at time t, $v_i$ is the initial velocity, and $k_{obs}$ is the apparent first-order rate constant for enzyme inactivation. The $k_{obs}$ were plotted versus inhibitor concentration and fitted to the equation $k_{obs}=k_{inact}[1]/(K_{app}+[1])$, where $K_{app}$ is the apparent dissociation constant of the reversible enzyme-inhibitor complex, and $k_{inact}$ is the first-order rate constant for apparent irreversible conversion of the enzyme-inhibitor complex to covalently bound complex. $K_i$ values were calculated using the equation $K_i=K_{app}/(1+[tryptophan]/K_{m,Trp})$ using experimentally determined $K_m$ values for tryptophan (Schirmer et al., *Proc. Natl. Acad. Sci. USA*, 103(11):4234-4239 (2006)).

X-Ray Crystallography

Crystals of RUMGNA_01526 were grown at room temperature in hanging drops consisting of equal volumes (1+1 mL) of 10 mg/mL RUMGNA_01526 and a crystallization solution composed of 0.1 M Bicine pH 8.5 and 25% PEG 3350. Crystals of RUMGNA_01526 with (S)-α-FMT were grown at room temperature in sitting drops consisting of equal volumes of 10 mg/mL RUMGNA_01526 pre-mixed with 5 mM (S)-α-FMT and a crystallization solution composed of 30% ethoxyethanol, 0.1 M citrate pH 5.25, and 4% polypropylene P400.

Structure Determination and Refinement

Crystals were flash-frozen in liquid nitrogen with 10% glycerol supplemented as a cryoprotectant. Data were collected on beamline 8.3.1 at the Advanced Light Source (Table 1). X-ray reflections were processed using xia2. All subsequent molecular replacement and structure analysis was performed using the PHENIX software suite. For the structure of RUMGNA_01526 in its native form, a molecular replacement search ensemble was created from the homologous models 2JIS, 3RBF, 4E1O, 3RCH, 2QMA, and 1JS3 using Phenix.sculptor and Phenix.ensembler. The structure of RUMGNA_01526 in its native form was used as a molecular replacement search model for the (S)-α-FMT-bound structure. All visualization components were performed using COOT.

TABLE 1

Data collection and refinement statistics.

| Wavelength (Å) | Apo-RUMGNA_01526 | S-aFMT-RUMGNA_01526 |
|---|---|---|
| Resolution range (Å) | 79.37-2.804 (2.805-2.804) | 52.44-2.84 (2.942-2.84) |
| Space group | P 1 | P 41 21 2 |
| Unit cell | 58.63 145.77 165.07 72.85 88.84 88.3 | 135.03 135.03 249.8 90 90 90 |
| Total reflections | 218936 (22174) | 730528 (73919) |
| Unique reflections | 121102 (12262) | 55248 (5448) |
| Multiplicity | 1.8 (1.8) | 13.2 (13.6) |
| Completeness (%) | 94.70 (96.28) | 99.97 (99.96) |
| Mean I/sigma(I) | 9.54 (2.09) | 25.80 (3.80) |
| Wilson B-factor | 41.16 | 54.76 |
| R-merge | 0.08033 (0.363) | 0.119 (0.8652) |
| R-meas | 0.1136 | 0.1238 |
| CC 1/2 | 0.99 (0.73) | 0.999 (0.881) |
| CC* | 0.998 (0.919) | 1 (0.968) |
| R-work | 0.2311 (0.3077) | 0.2098 (0.2745) |
| R-free | 0.2568 (0.3623) | 0.2423 (0.3494) |
| Number of atoms | 29598 | 15146 |
| macromolecules | 29064 | 14886 |
| ligands | 120 | 184 |

TABLE 1-continued

Data collection and refinement statistics.

| Wavelength (Å) | Apo-RUMGNA_01526 | S-aFMT-RUMGNA_01526 |
|---|---|---|
| Water | 414 | 0 |
| Protein residues | 3696 | 1889 |
| RMS(bonds) | 0.002 | 0.007 |
| RMS(angles) | 0.67 | 0.64 |
| Ramachandran favored (%) | 96 | 95 |
| Ramachandran outliers (%) | 0 | 0.053 |
| Clashscore | 3.03 | 3.04 |
| Average B-factor | 21.2 | 36.4 |
| macromolecules | 21.3 | 36.2 |
| ligands | 41.8 | 47.9 |
| solvent | 9.7 | |

Statistics for the highest-resolution shell sre shown in parentheses.

Ion Secretion from the Murine Colon

Figure 6:
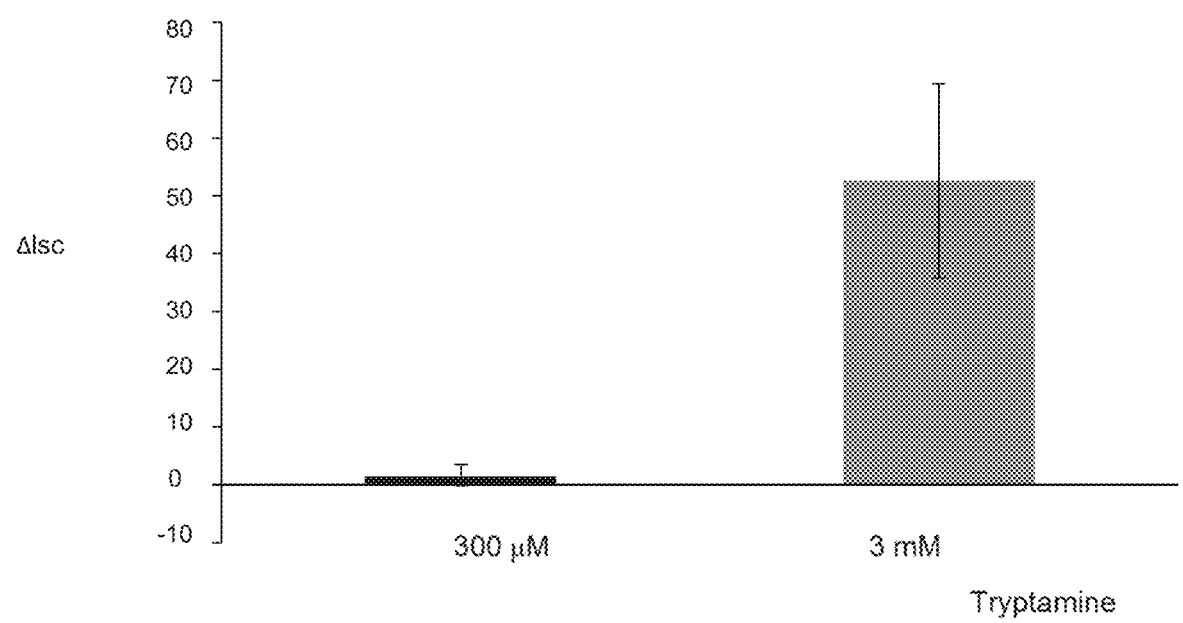
FIG. 6 shows tryptamine stimulates ion secretion by intestinal epithelial cells. Segments of proximal-mid colon, stripped of external muscle layers, were exposed to either 300 µM or 3 mM tryptamine using the Ussing chamber. The change in short circuit current was determined. A significant increase in ion secretions was observed in the presence of 3 mM, but not 300 µM tryptamine.

A segment of proximal-mid colon, stripped of external muscle layers from each of three SvEv129 mice was mounted in 0.3 cm² area, 4 mL Ussing chamber. Change in short circuit current (ΔIsc) was determined in response to two concentrations of tryptamine (300 M and 3 mM) on the mucosal side to mimic bacterially produced tryptamine and showed change in short circuit current representing intestinal secretion at 3 mM, but not at 300 µM. (FIG. 6).

Phylogenetic Analysis of Microbial Decarboxylases

Multiple sequence alignments were generated using MAFFT server (Katoh et al., *Methods in Molecular Biology*, 1079:131-146 (2014)), using Mafft-homologs function and the Blosum62 scoring matrix. Additionally, a structure-based sequence alignment of four decarboxylases (the holo structure of RUMGNA_01526 presented here and the following three structures from the: 3F9T, 3FZ8, and 4E10) was used as a constraint in the alignment procedure. The structure-based sequence alignment was generated by "Match→Align" function in Chimera (Pettersen et al., *J. Comp. Chem.*, 25(13):1605-1612 (2004)), followed by manual refinement. The phylogenetic tree was generated using the PHYLIP Neighbor Joining method (http://evolution.genetics.washington.edu/phylip.html), with the Jones-Taylor-Thornton distance matrix model.

Metagenomic Analysis of Decarboxylase Prevalence

Protein databases of all assembled metagenomic data of the Human Microbiome Project stool samples were accessed through HMP Data Analysis and Coordination Center. BLASTP searches were performed using RUMGNA_01526 and CLOSPO_02083 as query sequences, with a cutoff expectation value of 1 e$^{-50}$ in protein sequences bigger than 100 amino acids. Hits were then analyzed further by comparing them to the NCBI protein database using BLASTP and determining their closest homologs in sequenced microbial genomes.

Results

*Clostridium sporogenes* Decarboxylates Tryptophan to Tryptamine

In an effort to characterize the primary products to which tryptophan (Trp) was converted, the common gut Firmicute *Clostridium sporogenes* ATCC 15579 were cultivated in rich medium. Then, the cell material was transferred into minimal medium to which Trp had been added. In extracts of these cultures, reverse-phase HPLC-MS analysis revealed an unexpected conversion product that was distinct from the known products of reductive Trp metabolism, indole lactic acid and indole propionic acid (FIG. 1). Since the mass of the unknown peak corresponded to the loss of the carboxylic acid group from Trp ([M+H]+m/z: calculated 161.22, observed 161.12), the identity of this compound was tested and confirmed to be tryptamine by co-injection with an authentic standard and by comparison of its 1H NMR spectrum to that of an authentic standard (FIG. 2A). Notably, the presence of tryptamine in the culture fluid of *C. sporogenes* indicated that tryptamine was not only being produced but also excreted from the cytoplasm to the extracellular space.

Identification of CLOSPO_02083 as a Trp Decarboxylase

The enzyme responsible for Trp decarboxylation in *C. sporogenes* ATCC 15579 was identified. The two enzyme classes most commonly associated with amino acid decarboxylation are the pyridoxal 50-phosphate (PLP)-dependent decarboxylases, in which the catalytic cycle begins with the covalent linkage of the substrate a-amine to PLP as a Schiff base (John et al., *Biochim. Biophys. Acta* 1248:81-96 (1995); and Schneider et al., Structure 8:R1-R6 (2000)), and the pyruvoyl-dependent decarboxylases, in which a covalently bound pyruvoyl cofactor arises from an autocatalytic post-translational modification (Gallagher et al., *J. Mol. Biol.* 230:516-528 (1993); van Poelje and Snell, *Annu. Rev. Biochem.* 59:29-59 (1990)). A computational search of the *C. sporogenes* ATCC 15579 genome sequence revealed three putative PLP-dependent decarboxylases, but no putative pyruvoyl-dependent enzymes.

Figure 3A:
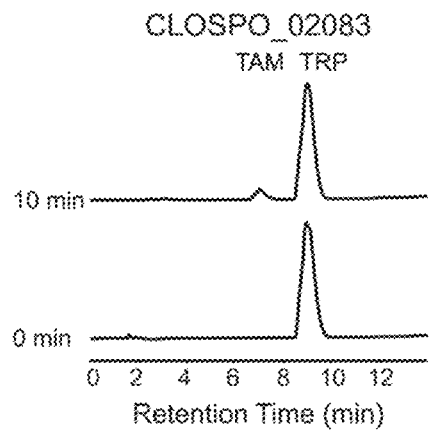
FIGS. 3A-3D show CLOSPO_02083 and RUMGNA_01526 are Trp decarboxylases. (A) Purified CLOSPO_02083 (100 nM) was incubated with 2.5 mM tryptophan for 10 minutes and quenched with 1 volume MeOH; 100 mL of the reaction mixture was analyzed by HPLC. The HPLC trace shows the conversion of tryptophan (TRP, 9 minutes) to tryptamine (TAM, 7 minutes). (B) R. gnavus was grown anaerobically in minimal media containing 5 g/L tryptophan; 100 mL of the clarified supernatant was analyzed by HPLC. The HPLC trace shows the conversion of tryptophan (TRP, 12.5 minutes) to tryptamine (TAM, 10.9 minutes). Different HPLC methods were used for (A) and (B). (C and D) Rate (mM tryptamine/minute) versus substrate concentration curves are provided for tryptophan decarboxylation by (C) CLOSPO_02083 or (D) RUMGNA_01526. Enzyme was incubated with concentrations of tryptophan that varied from 0.15-24.5 mM. Error represents standard error of the mean. GraphPad was used to fit the Michaelis-Menten curve.

None of the three genes was annotated as Trp decarboxylases. CLOSPO_02083 was predicted to be a tyrosine (Tyr) decarboxylase, while CLOSPO_03076 and CLOSPO_00504 were predicted to be glutamate decarboxylases. CLOSPO_02083 was characterized, hypothesizing that its annotation might be correct and Trp decarboxylation was a secondary activity—or incorrect but close, since Tyr and Trp are both aromatic amino acids. The CLOSPO_02083 gene was amplified by PCR from *C. sporogenes* genomic DNA, subcloned into the pET-28a expression vector, and heterologously overexpressed in *E. coli* BL21 (DE3) as an N-terminal His6 fusion protein. CLOSPO_02083 fusion protein was purified by immobilized nickel affinity chromatography to >95% homogeneity (FIG. 2B). When CLOSPO_02083 was incubated with Trp for 6 minutes at 37° C., HPLC analysis of the reaction mixture revealed a new peak (FIG. 3A). The identity of the corresponding compound was consistent with tryptamine by coelution with an authentic standard.

Kinetic Analysis of CLOSPO_02083 Activity with Aromatic Amino Acid Substrates

The obtained result revealed that CLOSPO_02083 is capable of decarboxylating Trp, but it does not rule out the possibility that one of the other aromatic amino acids is transformed more efficiently.

Figure 3B:
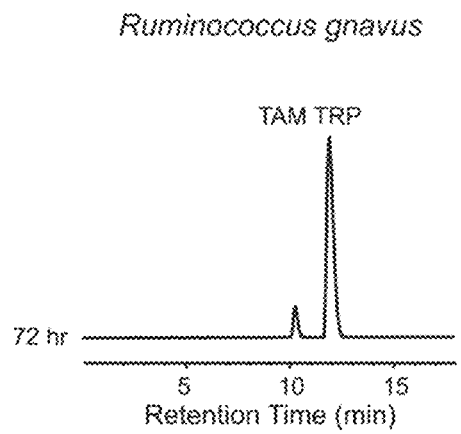
Figure 3C:
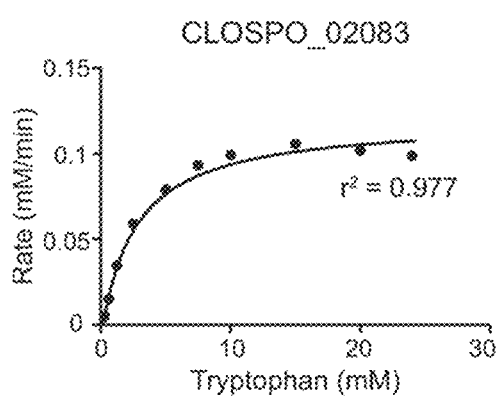
Figure 4A:
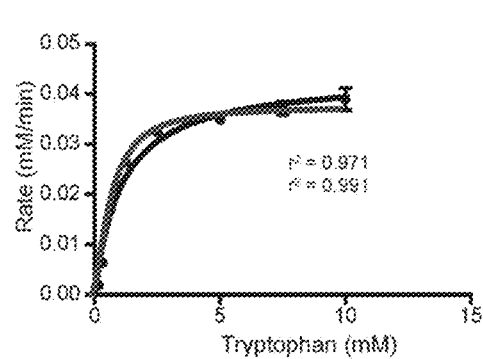
FIGS. 4A-4C show rate (mM tryptamine/minute) vs substrate concentration curves for (A) tryptophan or (B) phenylalanine decarboxylation by RUMGNA_01526. 100 nM enzyme incubated with tryptophan varied from 0.15-24.5 mM. GraphPad was used to fit the Michaelis-Menten (black) and Hill (gray) equations. (C) Allosteric site shows free (S)-α-FMT buried in a hydrophobic pocket near the N-terminus of the enzyme.

To gain insight into the substrate selectivity of CLOSPO_02083, the basic kinetic parameters were measured for CLOSPO_02083-catalyzed decarboxylation of the aromatic amino acids Trp, Tyr, and phenylalanine (Phe). To determine $k_{cat}$ and $K_m$ for CLOSPO_02083, the concentration of the amino acid substrate was varied under initial velocity conditions (FIGS. 3C and 4A). Trp is a robust substrate for decarboxylation CLOSPO_02083 with a $K_m$ of 2.8±0.0 mM, $k_{cat}$ of 1200 min$^{-1}$ and $k_{cat}/K_m$ of 7.3×10$^3$ M$^{-1}$ sec$^{-1}$. The activity of CLOSPO_02083 against Phe was undetectable up to 90 mM substrate (FIG. 2C). The limited solubility of Tyr did not allow one to obtain kinetic parameters. At the highest concentration of Tyr tested, CLOSPO_02083 was 600-fold more efficient at decarboxylating Trp (FIG. 2D). Collectively, these results show that Trp was accepted more efficiently as a substrate than Phe or Tyr.

These results demonstrate that the database annotation of CLOSPO_02083 as a Tyr decarboxylase is incorrect. The chemical distinction between Tyr and Trp is mild, since they are both aromatic amino acids. However, the biological distinction between their decarboxylation products is sharp. Tyramine stimulates a pressor response that results in an increase in blood pressure (Bianchetti et al., *Klin. Wochenschr.* 60:465-470 (1982)), whereas tryptamine induces the release of serotonin from enterochromaffin cells and stimulates GI motility (Takaki et al., *Neuroscience,* 16:223-240 (1985)). Thus, a modest difference in a decarboxylase's substrate selectivity can lead to entirely distinct biological outcomes, placing a premium on biochemically characterizing the substrate selectivity of amino acid decarboxylases expressed by gut commensals.

A Phylogenetic Analysis of Bacterial Decarboxylases to Select a Functionally Diverse Set of 15 Candidate Enzymes Several other gut-associated *Clostridium* spp. harbor a homolog of CLOSPO_02083, but this enzyme does not appear to be present in other gut Firmicutes. The following was performed to determine whether additional unrelated Trp decarboxylases exist among the human microbiota. The only putative tryptophan decarboxylases in the NCBI databases came from plant and fungal genomes, but the fact that CLOSPO_02083 was mis-annotated as a Tyr decarboxylase led to the hypothesis that there might be other mis- or unannotated decarboxylases encoded by the microbiota that are Trp selective.

Figures 5A, 5B:
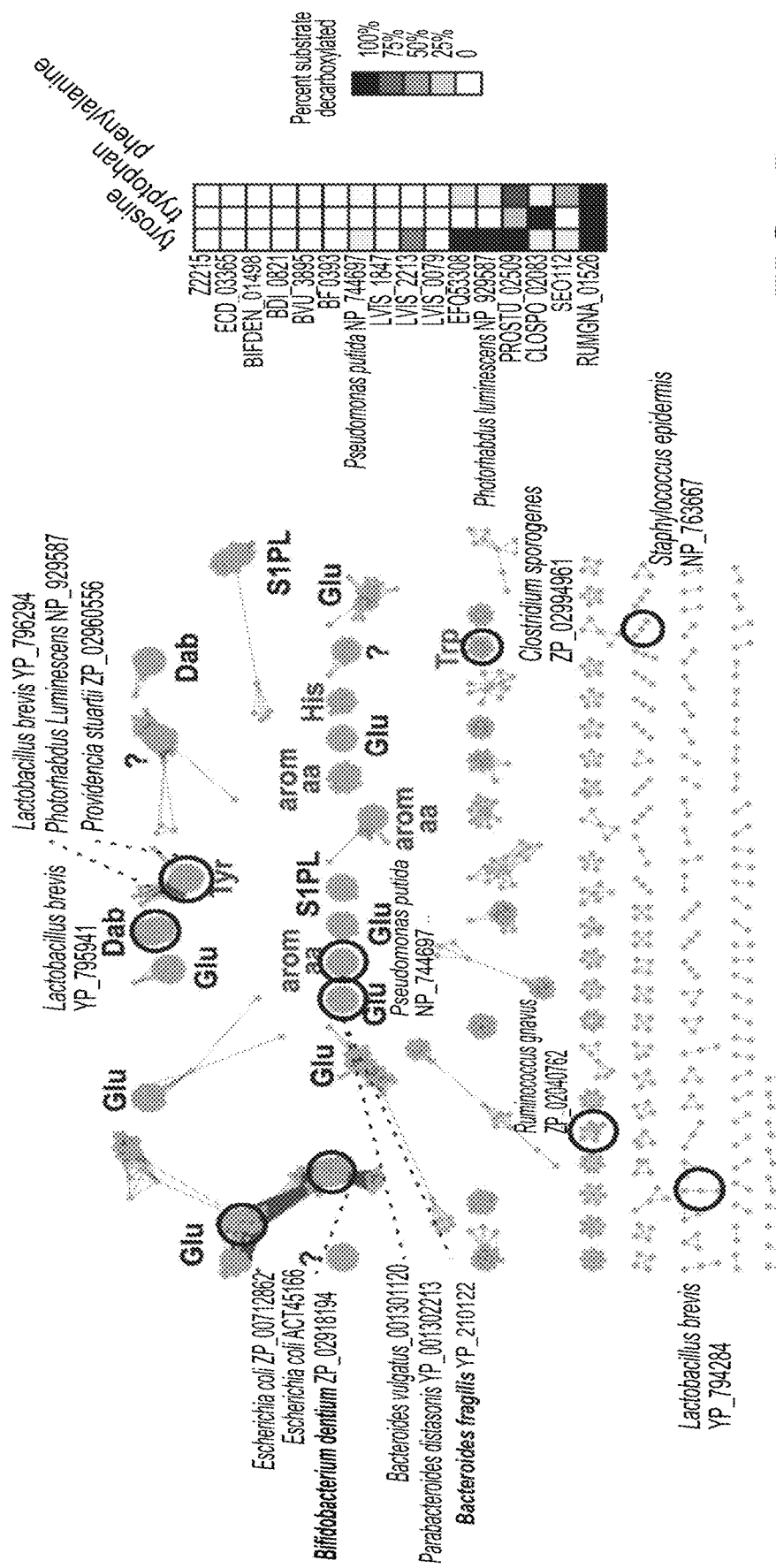
FIGS. 5A-5B shows cytoscape clustering of pfam00282 containing sequences in the jgi database and activity of selected enzymes. (A) The pfam consensus sequence for PLP-dependent decarboxylases (PLP_dec, pfam00282) was used as a query in a BLAST search against the JGI database and hits were clustered based on similarity. Clusters were labeled with predicted substrates. The included genes were selected to represent several clusters and were labeled. (B) A summary of decarboxylase activity is provided. Genes were cloned into pET-28a and expressed in E. coli BL21 in the presence of tryptophan, tyrosine, or phenylalanine for 24 hours. Percent decarboxylation was determined by dividing the integrated peak area (AUC) of the amine by the sum of the AUC of both the amine and acid, and represented in gray scale.

To select a small panel of candidate decarboxylases from the microbiota, a phylogenetic analysis of bacterial decarboxylases in which protein sequences were grouped into clades in which members are predicted to share a similar (if not identical) substrate selectivity was performed. Then, 15 enzymes were selected for characterization in a manner that maximized the ability to search the functional space of microbiome decarboxylases. At least one sequence from each of the largest clades and three additional sequences from smaller clades (FIG. 5A). Each of the host organisms were obtained and cultivated to isolate genomic DNA. The candidate decarboxylases were amplified by PCR, subcloned into the pET-28a expression vector, and heterologously overexpressed in *E. coli* BL21 as N-terminal His6 fusion proteins.

A Phylogeny-Informed Screen for Additional Trp Decarboxylases from the Microbiota Since the aim was to discover Trp decarboxylases rather than to obtain kinetic parameters for each enzyme in the screening panel, a whole-cell assay was developed and employed to assess rapidly the substrate selectivity of the candidate decarboxylases. *E. coli* BL21 (DE3) harboring candidate decarboxylases in pET-28a expression vectors were cultivated in rich medium and grown to stationary phase. The cells were transferred into minimal medium containing an aromatic amino acid substrate (Trp, Tyr, or Phe), and decarboxylation was monitored by analyzing cell-free culture fluid by analytical HPLC. This assay takes advantage of the fact that β-arylamines, the products of decarboxylase activity in the *E. coli* cytoplasm, could be detected in the extracellular fluid of *E. coli* cultures being screened and were not produced by wild-type *E. coli*.

This qualitative assay allowed 15 decarboxylases to be screened against three substrates (FIG. 5B). One of the enzymes screened, RUMGNA_01526, appeared to be capable of decarboxylating Trp robustly. Notably, this enzyme was only very distantly related to CLOSPO_02083 (26% amino acid sequence identity). To confirm this result biochemically, RUMGNA_01526 fusion protein was purified by immobilized nickel affinity chromatography to >95% homogeneity (FIG. 2B).

RUMGNA_01526 Is a Trp Decarboxylase

Figure 3D:
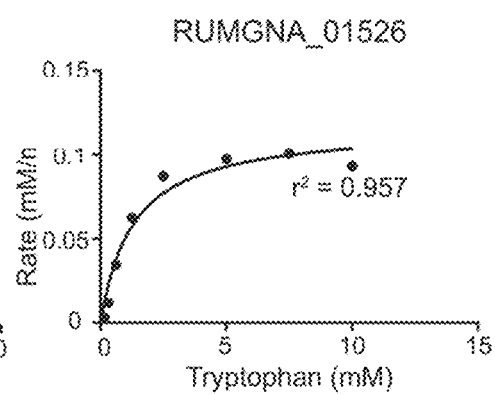

Basic kinetic parameters were measured for the decarboxylation of Trp, Tyr, and Phe by RUMGNA_01526. As shown in FIG. 3D, Trp is a robust substrate for decarboxylation, with a $k_{cat}$ of 4400 min$^{-1}$, a $K_m$ of 1.1±0.1 mM, and a $k_{cat}/K_m$ of $6.8 \times 10^4$ M$^{-1}$ sec$^{-1}$. In spite of the robust activity of RUMGNA_01526 against Trp, Tyr, and Phe in the cell-based assay, the catalytic efficiency of RUMGNA_01526 for Trp is >1000-fold higher than it is for Phe (FIGS. 3D and 4B), due to the combination of a higher $k_{cat}$ (19-fold) and a lower $K_m$ (70-fold). Although the limited solubility of Tyr prevented obtaining kinetic parameters, at the highest concentration of Tyr tested, RUMGNA_01526 was 1000-fold more efficient at decarboxylating Trp. These data demonstrate that tryptophan is the native substrate of RUMGNA_01526 (FIGS. 2C and 2D).

*R. gnavus* Excretes Tryptamine into the Extracellular Fluid

FIG. 1B showed that *C. sporogenes* excretes the tryptamine generated by CLOSPO_02083 into the culture fluid. However, tryptamine produced in the cytoplasm could have a variety of alternative intracellular fates, including serving as a building block for the synthesis of a larger molecule. Having shown that RUMGNA_01526 is a Trp decarboxylase, it was asked whether *R. gnavus* excretes the tryptamine from RUMGNA_01526 into the extracellular space. *R. gnavus* was cultivated in rich medium until stationary phase, transferred the cell material into a defined medium in the absence or presence of added Trp, and monitored the extracellular fluid by analytical HPLC. After 72 hours it the concentration of tryptamine reached ~1.7 mM (FIG. 3B) showing that *R. gnavus* excretes tryptamine in vitro and demonstrating that this strain can excrete tryptamine in the ecological setting of the gut lumen.

Tryptamine Induces Ion Secretion by Intestinal Epithelial Cells

The function of tryptamine in the context of microbe-host signaling in the gut was examined. An experiment to test whether tryptamine is capable of inducing ion secretion by intestinal epithelial cells was performed. Using an Ussing chamber, a segment of proximal-mid murine colon mucosa was exposed to two concentrations of tryptamine and the change of short circuit current was measured. At 3 mM, a concentration comparable to the active concentration of other bacterial fermentation products such as short-chain fatty acids, tryptamine induced a significant change in short circuit current, confirming that it can affect colonic ion secretion (FIG. 6). Since colonic ion secretion plays an important role in gastrointestinal motility, this result demonstrates that tryptamine-mediated signaling can affect the transit of food particles and bacterial cells through the gut lumen.

RUMGNA 01526Is a Fold Type I PLP-Dependent Decarboxylase

Figure 7A:
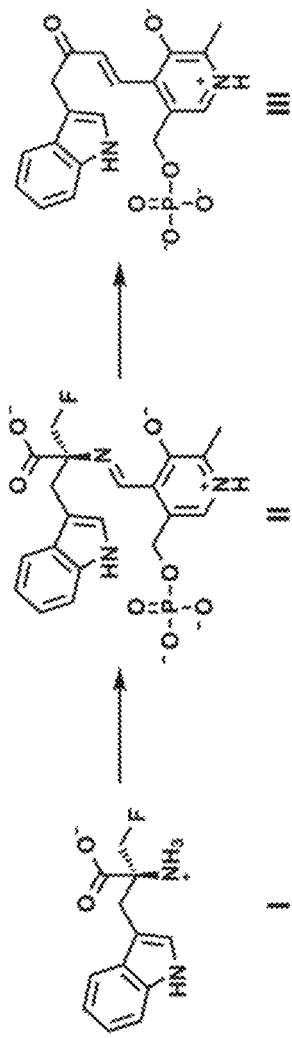
FIGS. 7A-7D show a crystal structure of apo and ligand-bound RUMGNA_01526. (A) Schematic of proposed inhibitor mechanism: (S)-α-FMT (I) is converted to a PLP-(S)-α-FMT external aldimine intermediate (II), which undergoes decarboxylation, fluoride ion elimination, and transaldimination to form a PLP-(S)-α-FMT ketone adduct (III). (B) Overlay of ligand-free (monomer A, light gray; monomer B, dark gray) and ligand-bound (monomer A, medium gray; monomer B, dark gray) structures. In the active and allosteric sites, PLP-(S)-α-FMT and (S)-α-FMT (respectively) are shown in spheres. (C) Active site with PLP-(S)-α-FMT bound reveals a repositioning of Tyr335 and Phe98. In the ligand-bound structure, Lys306 is no longer covalently bound to PLP. (D) Upon engagement of (S)-α-FMT, residues 337-349 (dark gray spheres) fold over the active site, excluding solvent and forming critical interactions with the inhibitor. Dark gray spheres represent only ordered residues in apo structure.
Figure 7C:
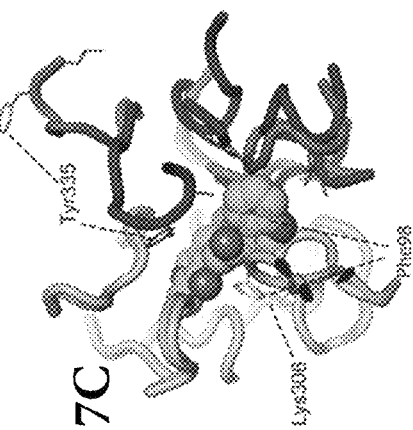
Figure 7C:
Figure 7B:
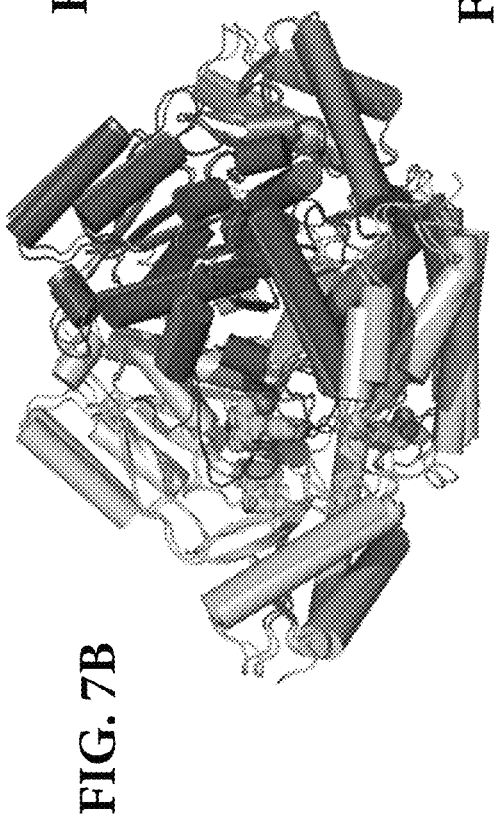

A combination of structural biology and phylogenetics to was used to examine the provenance of bacterial Trp decarboxylases. Crystals of CLOSPO_02083 in the apo form failed to diffract to an adequate resolution, but the crystal structure of RUMGNA_01526 at 2.8 Å was determined. The enzyme forms a dimer with 4565 Å$^2$ buried at the dimer interface. The active site is located at the dimer interface and therefore the enzyme is only functional in the dimeric state. The monomeric unit is comprised of three domains: an N-terminal domain containing three parallel α helices that pack against the other monomer, a large domain comprised of a nine-stranded β sheet surrounded by nine α helices containing the PLP-binding site, and a smaller C-terminal domain comprised of a four-strand anti-parallel R sheet surrounded by three α helices (FIG. 7B). The structure is nearly identical to the open form of human glutamate decarboxylase (GAD65), with an overall α-carbon RMSD of 1.07 Å (Fenalti et al., Nat. Struct. Mol. Biol. 14:280-286 (2007)). Similar comparisons can be made to human aromatic amino acid decarboxylase (Giardina et al., Proc. Natl. Acad. Sci. USA 108:20514-20519 (2011)) and wild boar DOPA decarboxylase (Burkhard et al., Nat. Struct. Biol. 8:963-967 (2001)), with α-carbon RMSDs of 1.21 Å and 1.23 Å, respectively. The agreement between these structures highlights the commonality of this enzymatic fold, even across multiple species.

(S)-α-Fluoromethyltryptophan Is an Inhibitor of RUMGNA_01526

The close structural relationship between RUMGNA_01526 and glutamate decarboxylase raises the question of how the structural scaffold of RUMGNA_01526 accommodates the large, hydrophobic substrate Trp. Since the ideal approach to answering this question would involve determining the structure of RUMGNA_01526 bound to a Trp-mimicking inhibitor, we proceeded to determine whether a previously reported inhibitor of plant Trp decarboxylase, (S)-α-fluoromethyltryptophan ([S]-α-FMT; FIG. 7A, I), was an inhibitor of RUMGNA_01526 (Ishihara et al., 2011 Phytochemistry 72:7-13).

Mechanistic studies have not been performed to determine the mode of Trp decarboxylase inhibition by (S)-α-FMT. Biochemical studies with a similar amino acid analog, (S)-α-fluoromethylhistidine ([S]-α-FMHI), show that this inhibitor blocks histidine decarboxylase in a mechanism-dependent fashion that involves the formation of a covalent adduct between the inhibitor and PLP.

The production of tryptamine was measured by HPLC in the presence of various concentrations of inhibitor over 30 minutes and progress curves of the reaction were analyzed to assess the kinetics of inhibition. For RUMGNA_01526 and CLOSPO_02083, progress curves consistent with covalent inhibition were observed in the presence of increasing concentrations of inhibitor (FIGS. 8A and 8B). Despite having a comparable $K_m$ for Trp, RUMGNA_01526 has a weaker affinity for (S)-α-FMT than CLOSPO_02083 ($K_i$ of 178 μM versus 0.2 μM). However, it is more rapidly inhibited ($k_{inact}$ of 1.2 min$^{-1}$ versus 0.1 min$^{-1}$), demonstrating that once the weak enzyme-inhibitor complex forms, the relative orientation of PLP and the inhibitor is conducive to covalent bond formation (FIGS. 8C and 8D).

Inactivation of histidine decarboxylase by (S)-α-FMH is initiated by substrate decarboxylation followed by the elimination of fluoride ion (Bhattacharjee and Snell, J. Biol. Chem. 265:6664-6668 (1990); Hayashi et al., J. Biol. Chem. 261:11003-11009 (1986)). A transaldimination releases the enamine that reacts with and inactivates the PLP cofactor. In order to elucidate the mechanism by which (S)-α-FMT inhibits RUMGNA_01526, as well as to understand how RUMGNA_01526 accommodates the large, hydrophobic substrate Trp, the X-ray crystal structure of the inhibitor-bound enzyme was determined.

Figure 7D:
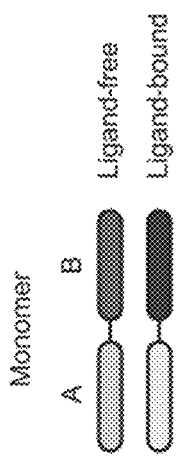

A Key Loop Gates the Active Site and Contacts the Indole Side Chain of the Substrate Trp The crystal structure of inhibitor-bound RUMGNA_01526 at 2.8 Å was determined. In the active site of the native enzyme, located in a cleft at the dimer interface, continuous electron density shows PLP covalently linked to K306 through a Schiff base. The major difference between the native and (S)-α-FMT-bound structures is the conformation of an extended loop (residues 337-349). The homologous loop was previously identified as a major difference between GAD65 and GAD67, where differences in conformational dynamics are thought to be responsible for auto-inactivation of GAD65 (Fenalti et al., Nat. Struct. Mol. Biol. 14:280-286 (2007)). In porcine DOPA decarboxylase, this loop was disordered in three data sets from complexes with different inhibitors, complicating structure-based drug design and an assessment of catalytic mechanisms (Burkhard et al., Nat. Struct. Biol. 8:963-967 (2001)). In contrast, it was observed that when bound to PLP alone, this loop was partially disordered and the remaining ordered components jutted away from the active site, leaving the active site solvent-exposed. Upon engagement of (S)-α-FMT, electron density became clearer and the loop folded over the active site, excluding solvent and forming critical interactions with the inhibitor (FIG. 7D, FIG. 4, and FIG. 9). These data are consistent with a model in which loop 337-349 gates the active site, adopting a partially disordered, outward-facing conformation in the absence of substrate that enables access to the active site, and closing down to cap the active site after substrate entry.

Two other flexible loops within the active site of the inhibitor-bound enzyme are reordered to accommodate the indole side chain of (S)-α-FMT. In the absence of substrate, the first loop (residues 95-101) leaves the active site accessible for the entry of a substrate with a large aromatic side chain. Upon substrate binding, the loop conformational change places the phenyl ring of Phe98 directly above the p-system of the indole ring, stabilizing the inhibitor through a p-stacking interaction (FIG. 7C). This loop appears to be a critical element for defining substrate selectivity; consistent with this possibility, it is conserved among decarboxylases in several related Firmicutes. The second loop, residues 329-336, reorients to shift the phenolic side chain of Tyr335 closer to the active site, increasing the hydrophobicity of the substrate-binding pocket.

Insights into the Mechanism of Inhibition by (S)-α-FMT and a Potential Allosteric Site In the inhibitor-bound structure, (S)-α-FMT has been decarboxylated; however, it has not been defluorinated as seen in the mechanism of (S)-α-FMH inhibition of histidine decarboxylase and remains covalently linked to PLP. This is supported by the absence of a suitable nucleophile in the active site that could be covalently modified by the defluorinated (S)-α-FMT-PLP adduct.

The (S)-α-FMT-PLP adduct (FIG. 7A, III) is relatively disordered in the electron density maps of both active sites; however, the maps show an absence of density consistent with a covalent linkage between PLP and the enzyme. To further probe the identity of the adduct, the enzyme was denatured after incubation with PLP and (S)-α-FMT and the released product was analyzed (FIGS. 9A-D). A single species of mass 403 was found which most likely represents the ketone formed after (S)-α-FMT is decarboxylated, defluorinated, and deaminated (FIG. 9B). The same adduct is also found during the inactivation of histidine decarboxylase by (S)-α-fluoromethylhistidine (Bhattacharjee and Snell, J. Biol. Chem. 265:6664-6668 (1990)). Collectively, these data indicate that the PLP-(S)-α-FMT adduct is formed and remains tightly bound rather than diffusing out of the active site. Thus, the blockade of RUMGNA_01526 by (S)-α-FMT appears to be an enzyme-catalyzed inactivation of the PLP coenzyme and does not involve a chemical modification of the enzyme itself.

Figure 4B:
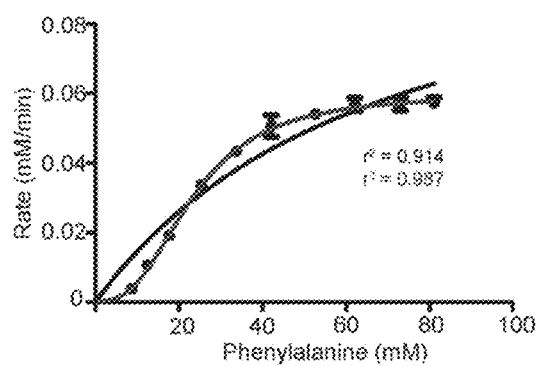
Figure 4C:
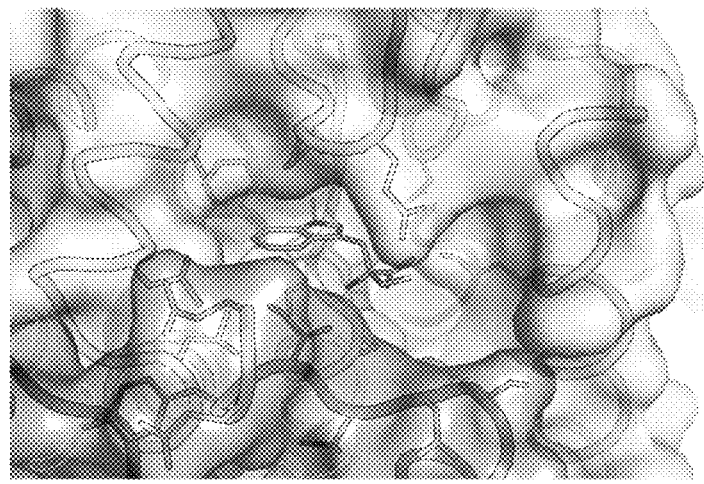
Figures 10A, 10B, 10C:
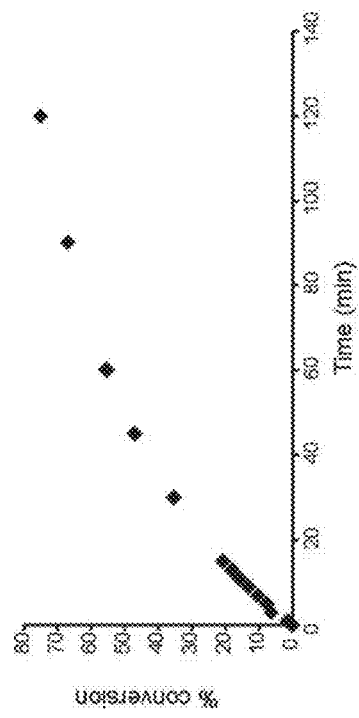
FIGS. 10A-10C shows a table of kinetic results. (A) Michaelis-Menten and (B) Hill equation kinetic parameters for CLOPSO_02083 and RUMGNA_01526 with tryptophan and RUMGNA_01526 with phenylalanine are provided. (C) A progress curve of tryptophan consumption by 10 nM RUMGNA_01526 in the presence of 1.25 mM tryptophan was generated.

An additional molecule of (S)-α-FMT was observed bound to a site ~20 Å from the active site (FIG. 4C). The inhibitor fits inside a hydrophobic pocket that is formed by the movement of an N-terminal loop (residues 16-22) and makes hydrogen bonds to S105 and the backbone of P102. While this binding event might be a crystallization artifact, the kinetic data are consistent with the possibility of cooperative substrate binding to an allosteric site as evidenced by a slight increase in the $r^2$ value for the fit to the Hill equation (Hill coefficient=1.87) versus the Michaelis-Menten equation (FIGS. 10, 4A, and 4B).

Figures 11A, 11B, 11C:
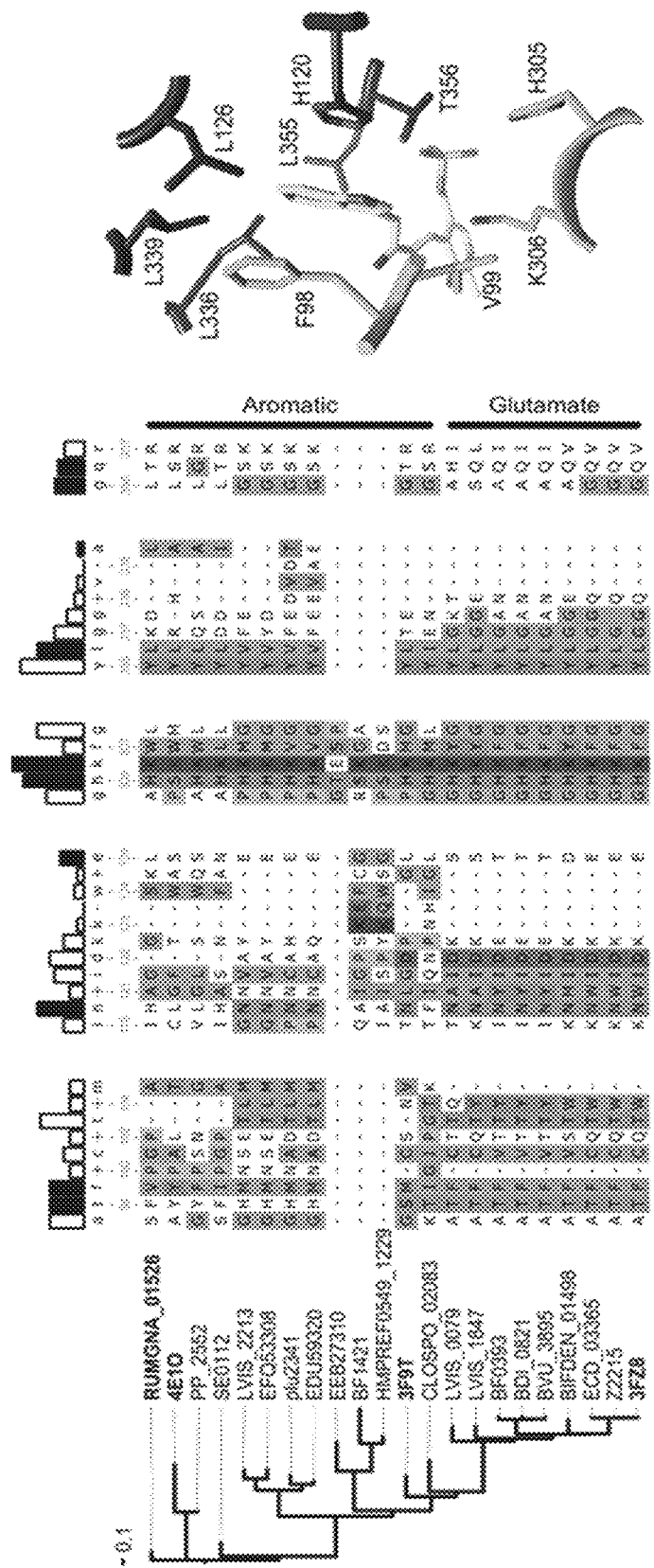
FIGS. 11A-11C show sequence and structural analysis of aromatic amino acid decarboxylases. (A) The dendrogram on the left shows the degree of sequence similarity between various decarboxylases. (B) Alignment of select amino acid decarboxylases are numbered according to the RUMGNA_01526 sequence (SEQ ID NO:1). Additional decarboxylase sequences shown include 4E10 (SEQ ID NO:2), PP_2552 (SEQ ID NO:3), SE0112 (SEQ ID NO: 4), LVIS_2213 (SEQ ID NO:5), EFQ53308 (SEQ ID NO:6), plu2341 (SEQ ID NO:7), EDU59320 (SEQ ID NO:8), EEB27310 (SEQ ID NO:9), BF1421 (SEQ ID NO:10), HMPREF0549_1229 (SEQ ID NO:11), 3F9T (SEQ ID NO:12), CLOSPO_02083 (SEQ ID NO:13), LVIS_0079 (SEQ ID NO:14), LVIS_1847 (SEQ ID NO:15), BF0393 (SEQ ID NO:16), BDI_0821 (SEQ ID NO:17), BVU_3895 (SEQ ID NO:18), BIFDEN_01498 (SEQ ID NO:19), ECD_03365 (SEQ ID NO:20), Z2215 (SEQ ID NO:21), and 3FZ8 (SEQ ID NO:22). Four structural components of RUMGNA_01526 involved in substrate binding are highlighted. The bars above the consensus sequence (SEQ ID NO:23) show the degree of sequence conservation; residues from the RUMGNA_01526 structure that interact (black bars) or do not interact (white) with the tryptophan substrate are indicated. Residues in the sequence alignment are colored according to the Clustal color code. (C) This panel shows RUMGNA_10526 active site residues represented by black bars in (B).

Evolutionary Insights from Sequence and Structure into the Substrate Selectivity and Origins of Bacterial Trp Decarboxylases The amino acid sequences of 21 enzymes were aligned: 15 decarboxylases from the phylogeny-informed screen, 3 annotated histidine decarboxylases, and 3 decarboxylases with known structure. Three notable patterns are apparent from the multiple sequence alignment. First, while the multiple sequence alignment shows a high degree of similarity between the amino-acid substrate binding sites of the glutamate decarboxylases, the binding sites that accommodate aromatic amino-acid substrates differ significantly (FIG. 11). With the exception of one enzyme (EEB27310), the only residue shared by all the sequences is K306, the active site lysine residue involved in binding PLP. Second, no apparent rules were found in the sequence alignment of the decarboxylases with aromatic amino acids as substrates that could explain their specificities or promiscuities for the aromatic amino acids; therefore, it is likely that the aromatic amino acid substrate specificity is governed by differences in the active site structures and/or orientations of the substrates. Even the serine residue at position 356 (354 in the original sequence) that was found to determine the histidine specificity of the human histidine decarboxylase (Komori et al., *J. Biol. Chem.* 287:29175-29183 (2012)) is found in other decarboxylases with no observed histidine activity. Third, the binding sites of decarboxylases with aromatic amino acid substrates are rich in proline residues, demonstrating that the specificity for different aromatic amino acid substrates could also be driven by active sites whose shapes match more rigidly those of the substrates.

Figure 12:
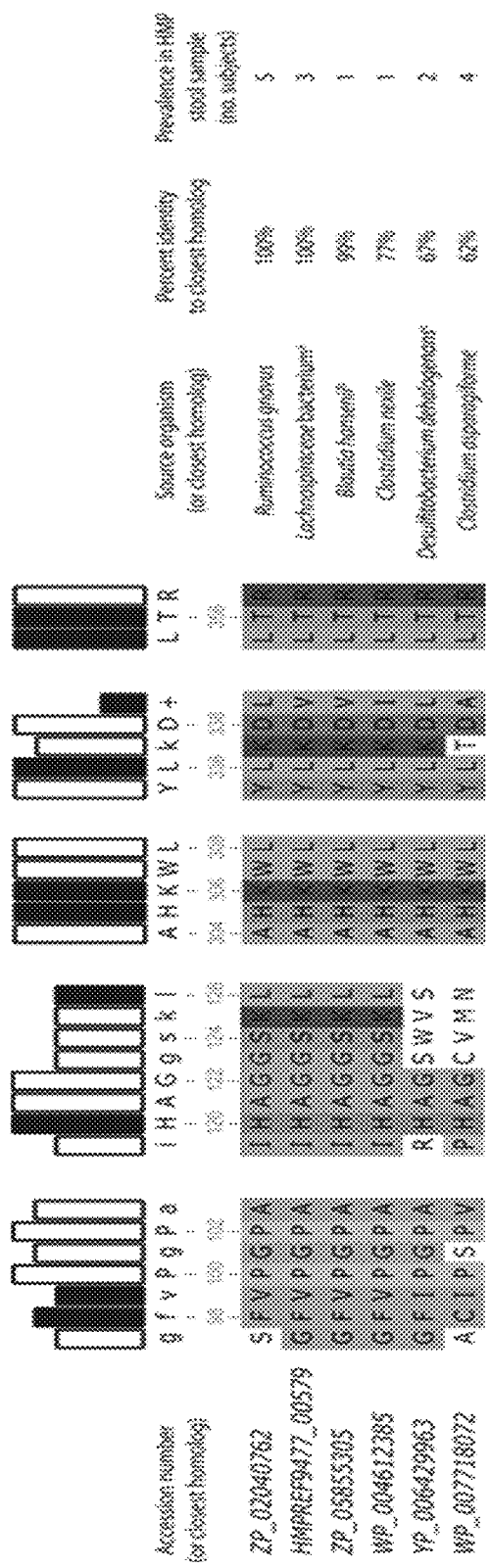
FIG. 12 shows presence of tryptophan decarboxylase in the human microbiome project samples accession numbers of proteins of highest sequence identity to RUMGNA_01526 (SEQ ID NO: 1; ZP_02040762). BLAST percent identity was calculated for at least 100 amino acids. Fifteen subjects were found to contain homologs of the putative tryptophan decarboxylases. Of those, two contained two different homologs, and 13 contained one homolog. One subject harbored a gene with 93% identity to either ZP_02040762 (SEQ ID NO:1) from *R. gnavus* or HMPREF9477_00579 (SEQ ID NO:24) from *Lachnospiraceae* bacterium 2_1_58FAA. A sequence alignment including accession numbers ZP_02040762 (SEQ ID NO:1), HMPREF9477_00579 (SEQ ID NO:24), ZP_05855305 (SEQ ID NO:25), WP_004612385 (SEQ ID NO:26), YP_006429963 (SEQ ID NO:27), and WP_007718072 (SEQ ID NO:28) was presented highlighting the residues identified by a structural analysis to be involved in accommodating tryptophan (black bars in the consensus sequence (SEQ ID NO:29)). (a) *Lachnospiraceae* bacterium 2_1_58FAA, (b) *Blautia hansenii* DSM 20583, and (c) *Desulfitobacterium dehalogenans* ATCC 51507.

Trp Decarboxylases Are Present in At Least 10⁰% of the Samples from the NIH Human Microbiome Project Initial assemblies of sequenced human stool samples from 86 healthy subjects were examined for the presence of similar amino acid decarboxylases. BLASTP to was used search the metagenomic contigs for homologs of RUMGNA_01526. Homologs of RUMGNA_01526 were identified in 15 subjects (17% of the samples). Of those, 13 subjects contained only one decarboxylase homolog, while two subjects harbored two different homologs. Eight subjects (9.3%) contained a Trp decarboxylase homolog that is almost identical to the RUMGNA_01526 characterized here (>99% identical at the amino acid level over >100 residues). The rest of the samples harbored decarboxylase homologs that were 62%-93% identical to RUMGNA_01526 over >100 residues (FIG. 12). A sequence alignment to RUMGNA_01526 shows nearly 100% identity over the residues critical for accepting tryptophan (FIG. 12). These homologs were highly similar to genes from a variety of anaerobic Firmicute reference genomes, such as *Clostridium asparagiforme*, *Clostridium nexile*, *Desulfitobacterium dehalogenans*, and *Blautia hansenii*. Despite the fact that *C. sporogenes* ATCC 15579 is a human gut isolate, similar searches with CLOSPO_02083 yielded no hits. The presence of Trp decarboxylase homologs in 9%-17% of gut metagenomes of a random population of healthy humans suggests that tryptamine produced by gut bacteria may be more prevalent in humans than previously thought.

These results and additional information are also described elsewhere (see, e.g., Williams et al., Cell Host & Microbe 16:495-503 (2014)).

Accession Numbers

Coordinates in the Protein Data Bank have been deposited with accession codes 4OBU (native RUMGNA_01526) and 4OBV (RUMGNA_01526-(S)-α-FMT complex).

Example 2: Acetate and Butyrate, but not Tryptamine, Reproducibly Modulate Tph1 mRNA Expression in BON Cells, a Model of Enterochromaffin Cells To determine if tryptamine can reproducibly and consistently stimulate serotonin synthesis in vitro tryptophan hydroxylase 1 (Tph1) mRNA expression was assessed in an alternate EC-like cell model-BON cells by qRT-PCR. Cells were plated at 1×10^5 per ml and grown to 90% confluency in 12-well culture plates. Culture wells were then treated (in triplicate) with tryptamine in media for 6 hours, fixed in RNA Protect (Qiagen) and subjected to qRT-PCR.

None of the tested tryptamine concentrations (1 μM, 5 μM, 10 μM, and 20 μM) reproducibly showed a significant alteration of Tph1 mRNA levels. Treatments with acetate of 10 mM, 30 mM, and 50 mM induced 2.5-fold, 3.2-fold and 2.2-fold Tph1 expression, respectively (P<0.001; One-way ANOVA; 2-3 independent experiments). The effect of another short chain fatty acid, butyrate, on Tph1 expression was also tested. Butyrate (500 M and 1 mM) induced Tph1 mRNA 3.5- and 2.5-fold above controls, respectively (P<0.05; 2-3 independent experiments).

These results demonstrate that tryptamine exerts physiological effects on the gut independent of serotonin.

Example 3: Open Organ Bath System Used to Measure Intraluminal Pressure of Mouse Colonic Segments Ex Vivo Following Infusion of Tryptamine Vs. Vehicle Preparations of full-thickness colonic segments (~1.5 cm) were allowed to equilibrate in 37° C. Kreb's-jacketed organ baths with their distal ends opening to a pressure transducer and maintained under basal pressure of 5-cm column of vehicle (RL). The proximal end was closed during pressure recordings but opened to allow luminal infusion of vehicle or tryptamine in solution (100 μM, 1 mM and 3 mM; 10 minutes per treatment; n=5-7 mice).

Contractile frequency was not significantly different comparing tryptamine treatments with vehicle controls; however, there was a trend toward increased frequency in segments treated with luminal 1 mM tryptamine compared to controls (5.9±0.8 vs 4.1±0.6; P=0.15). Mean contractile amplitude and contractile magnitude, as measured by area under the curve, were also not significantly different between control (vehicle alone) and any of the tryptamine concentrations examined. Contractile duration, measured at half amplitude, was not significantly different between vehicle controls and any of the luminal tryptamine treatments.

Example 4: Germ Free Mice and Humanized Mice Show Differential Epithelial Responses to Tryptamine, which can be Attenuated by 5HTR4 Receptor Antagonist but not 5HT3R Antagonists Two segments of proximal colon, stripped of external muscle layers from germ free (GF) and humanized mice (ex-GF colonized with human bacteria; HM) were mounted in 0.3 cm$^2$ area, 4 mL Ussing chambers. Colonic mucosal transepithelial resistance (TER) was measured at the beginning of each experiment and FITC Dextran (4 k Da) flux was determined from the linear fit of samples obtained from the serosal side every 5 minutes for 30 minutes after adding 1 mg/mL FITC-Dextran to the mucosal side. Change in short circuit current (Δlsc) was determined in response to electrical field stimulation (EFS) using foil electrodes on the submucosal side (30-150V, 100 0.5 ms pulses at 1-2 Hz). There was no significant difference in Δlsc between GF and HM in response to EFS at 1 Hz (138±42 vs 202±71 µA/cm$^2$; n=4; p>0.05) or 2 Hz (180±28 vs 252±70 µA/cm$^2$; n=4; p>0.05).

Acetylcholine (Ach) in increasing concentrations (0.01-300 µM) on the serosal side was used as a control for tissue reactivity. Cumulative concentration response curves induced by serosal ACh were not different between GF and HM as evident by similar Emax (261±38 vs 299±27 µA/cm$^2$; n=5; p>0.05) and $EC_{50}$ (20.6±3 vs 22.7±9 µM) values.

No differences in TER (50.2±1.7 vs 69.2±10.5 Ω/cm$^2$; n=4-5; p>0.05) or FITC dextran flux (2.4±0.5 vs 3.4±2 ng/mL/min/cm$^2$; n=4; p>0.05) were seen between GF and HM mice in response to 5HT (0.003-300 µM) on the mucosal or serosal side or in response to tryptamine (0.003-3000 µM) on the mucosal or serosal side.

Figure 13:
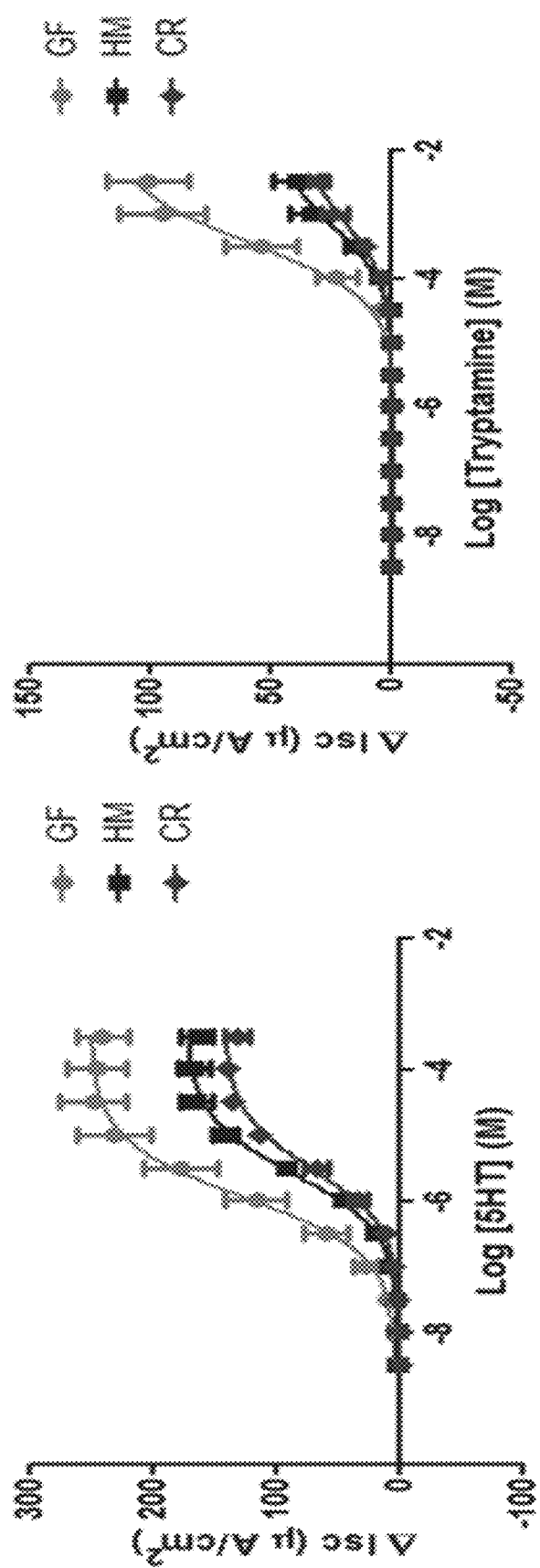
FIG. 13 shows graphs plotting changes in intestinal secretion in response to increasing concentrations of 5HT (left) or tryptamine (right) in germ free (GF), humanized (HM) and control (conventionally raised (CR)) mice.

Cumulative concentration response curves induced by serosal 5-HT were significantly higher in GF compared to HM and CR (FIG. 13).

Cumulative concentration response curves induced by serosal tryptamine were significantly higher in GF compared to HM and CR (FIG. 13).

Figure 14:
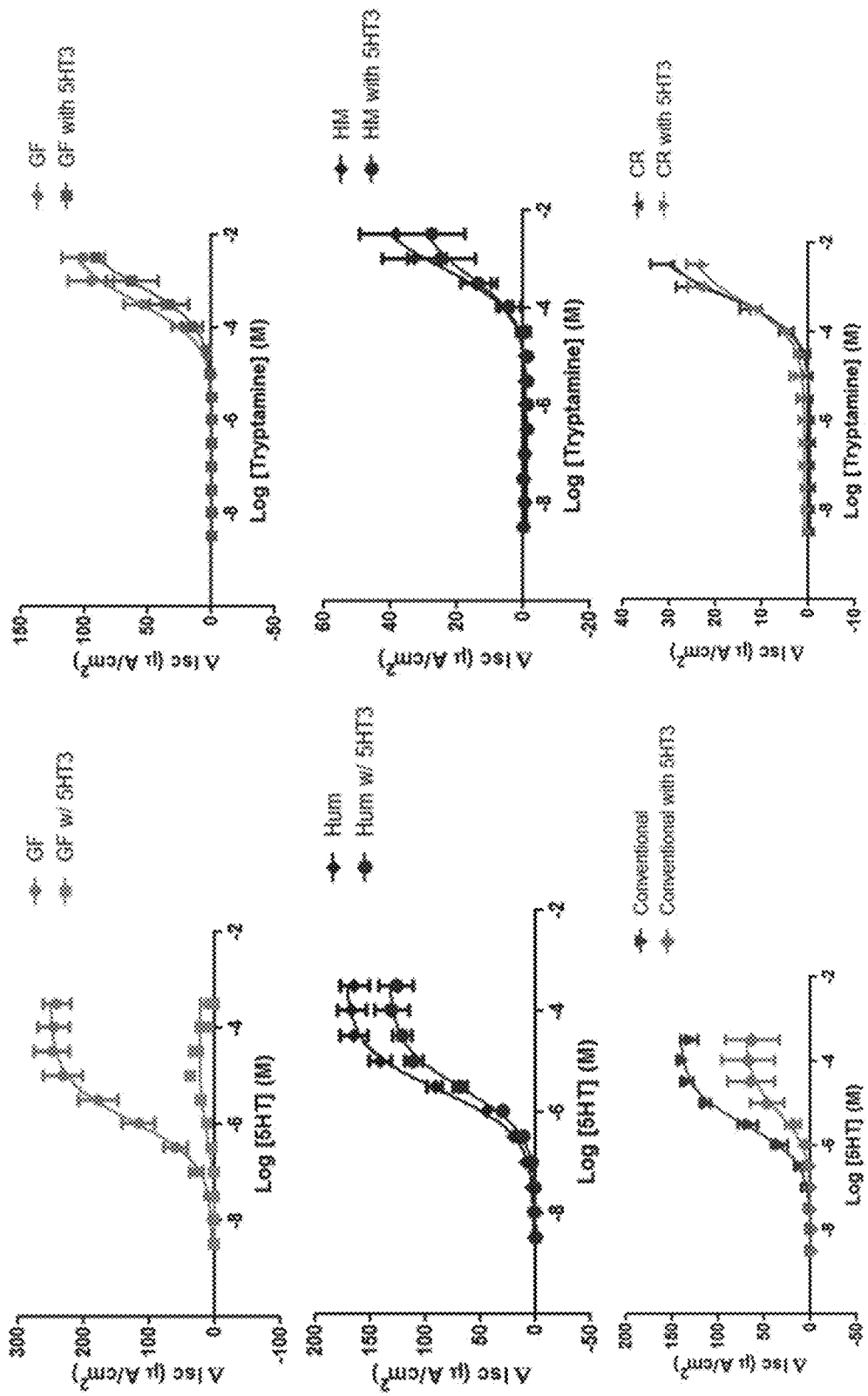
FIG. 14 shows graphs plotting changes in intestinal secretion in response to increasing concentrations of 5HT (left) or tryptamine (right) in the presence of 5HT3 in germ free (GF; top), humanized (HM; center) and control (CR; bottom) mice.
Figure 15:
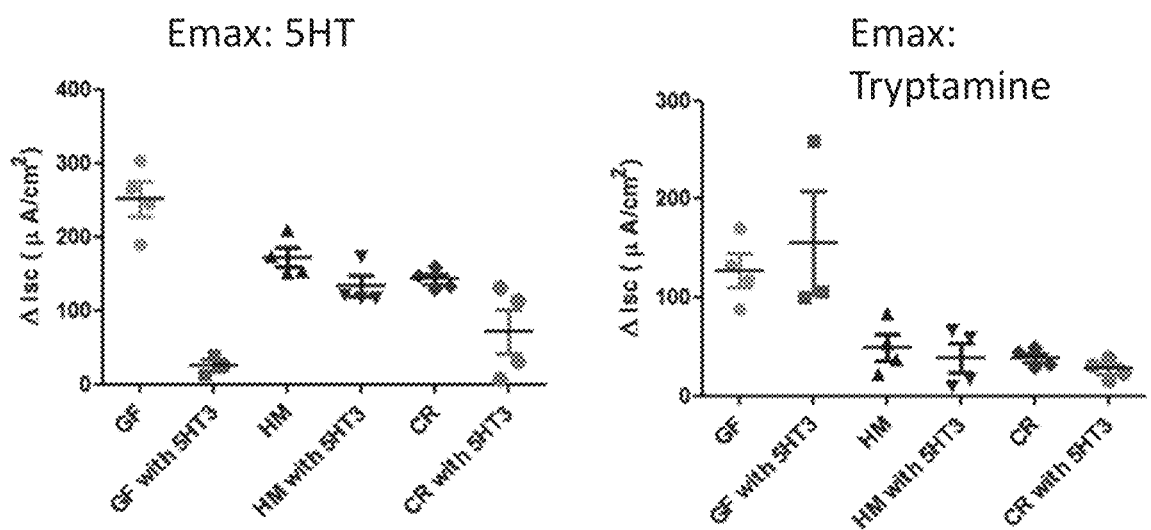
FIG. 15 shows graphs plotting maximal intestinal secretion in response to 5HT (left) or tryptamine (right) in the presence of 5HT3 in germ free (GF), humanized (HM) and control (CR) mice.

No change was seen in response to 5HT3 receptor antagonist. The 5HT3 receptor antagonist was applied with exogenous serotonin or with exogenous tryptamine to GF, HM, or conventionally raised (CR) mice (FIG. 14). Application of 5HT3 blocked the biological effect of exogenous serotonin, but did not block the exogenous effect of tryptamine. In addition, the maximal response ($E_{max}$) to exogenous serotonin can be blocked by 5HT3, but the maximal response to tryptamine is not blocked (FIG. 15).

Figure 16:
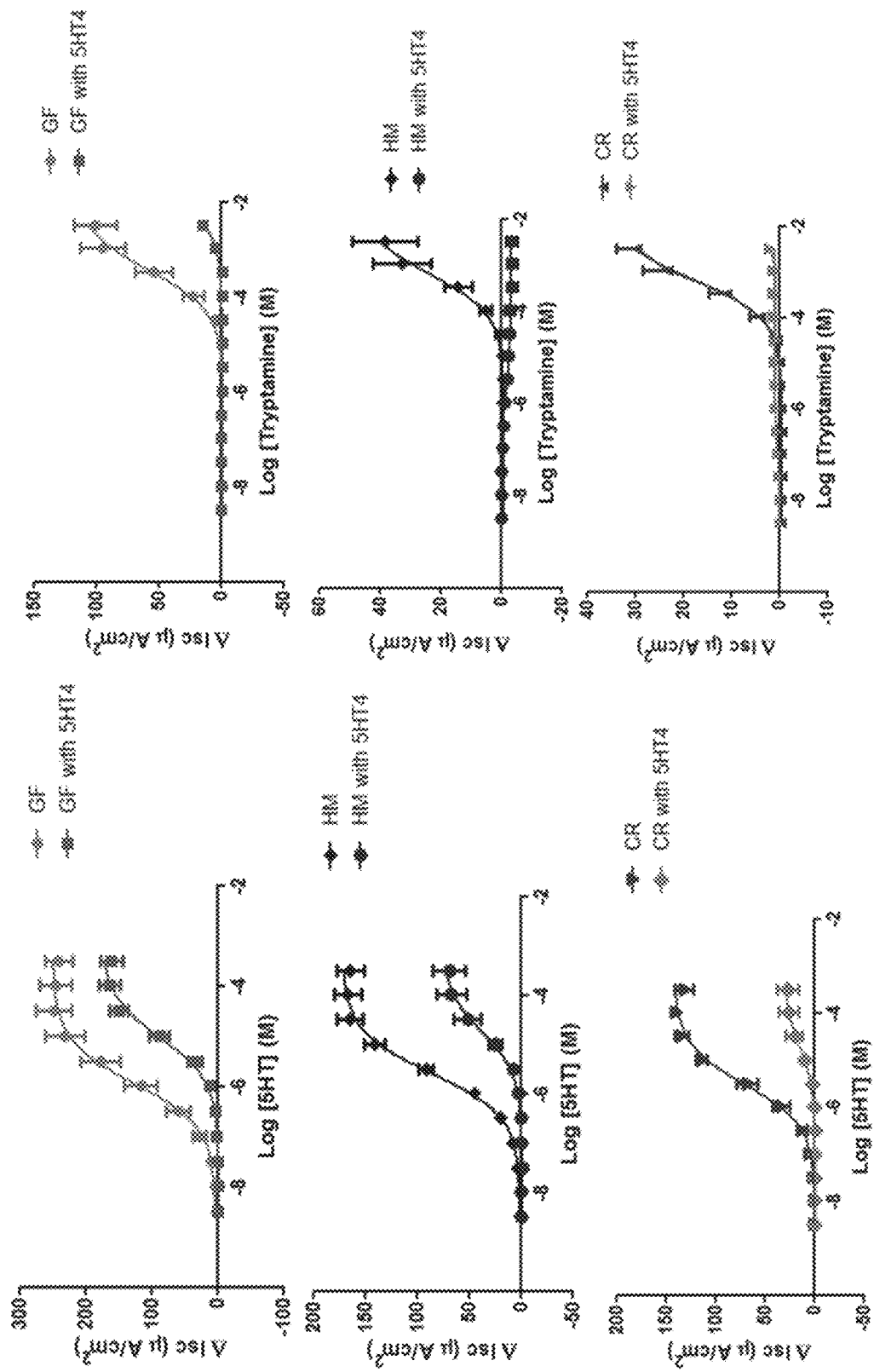
FIG. 16 shows graphs plotting changes in intestinal secretion in response to increasing concentrations of 5HT (left) or tryptamine (right) in the presence of 5HT4 in germ free (GF; top), humanized (HM; center) and control (CR; bottom) mice.
Figure 17:
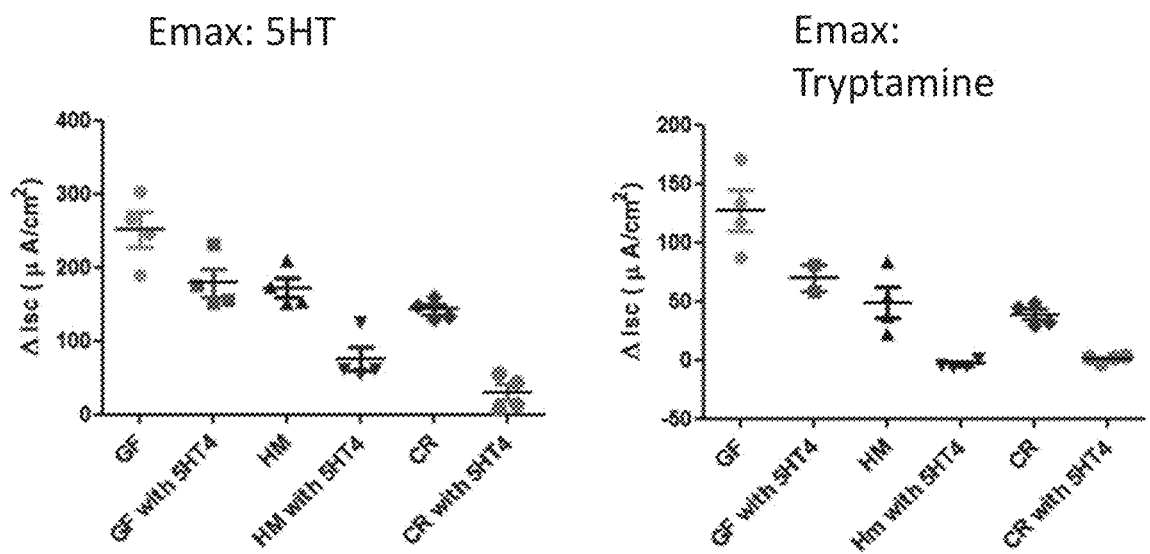
FIG. 17 shows graphs plotting maximal intestinal secretion in response to 5HT (left) or tryptamine (right) in the presence of 5HT4 in germ free (GF), humanized (HM) and control (CR) mice.

Application of 5HT4R on the mucosal and serosal side attenuated response to serotonin and tryptamine in mice irrespective of colonization state. The 5HT4 receptor antagonist was applied with exogenous serotonin or with exogenous tryptamine to GF, HM, or CR mice (FIG. 16). Application of 5HT4 blocked the biological effect of both exogenous serotonin and exogenous tryptamine. The maximal response ($E_{max}$) to both exogenous serotonin and exogenous tryptamine can be blocked by 5HT4 (FIG. 17).

These data show that GF mice have normal colonic epithelial cell function as well as normal responses to Ach and 5HT in the absence of gut microbiota making GF mice an excellent model system to study effects of individual microbes/microbial products on epithelial cell function. These results also show that tryptamine has a differential effect in GF, HM, and CR mice, that the effect of tryptamine can be blocked only by 5HT4 receptor antagonist, and that the effect of serotonin can be blocked by both 5HT3 and 4 receptor antagonist.

Example 5: Epithelial Responses to Tryptamine are Lost in 5HT4R Knock-Out Mice while they Remain Responsive to Serosal Application of 5HT The response to 5-hydroxytryptophan (5HT; 0.003-300 µM) on the mucosal or serosal side and tryptamine (0.003-3000 µM) on the mucosal or serosal side was determined in segments of proximal colon, stripped of external muscle layers, from both 5HTR4 KO and WT mice.

Figure 18:
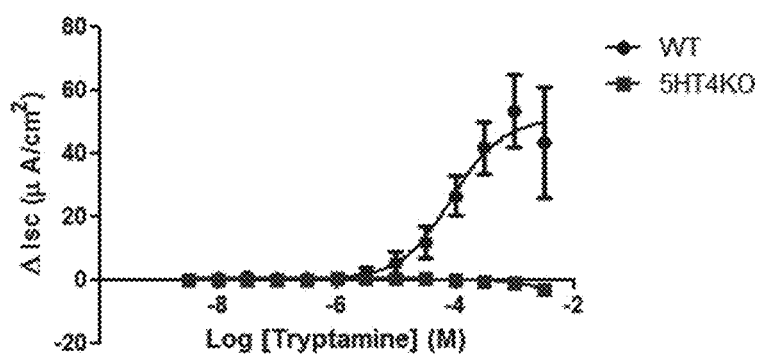
FIG. 18 shows a graph plotting changes in intestinal secretion in response to increasing concentrations of tryptamine in wild type (WT) and 5HT4 knock out (5HT4KO) mice.

Colon segments from 5HTR4 KO mice displayed decreased responsiveness to serosal serotonin and no response to mucosal serotonin when compared with colon segments from WT mice. Cumulative concentration response curves induced by serosal tryptamine were significantly different between 5HTR WT (Emax: 110±17 µA/cm2; n=6-7) and KO mice (no response). While Δlsc did not reach maximum response following mucosal application of 3000 µM tryptamine, responses were seen in 5HTR4 WT mice (99.5±30.7 n=5) while no response was elicited in 5HTR4 KO (FIG. 18).

These results show that tryptamine acts as a 5HTR4 mimetic with effects on gut epithelial function independent of serotonin.

Example 6: In Vivo Analysis of Gastrointestinal Epithelial Function

The organ bath system represents an ex vivo system lacking central nervous system (CNS) connections. Gastrointestinal motility is investigated using mice as an animal model. Experiments are performed to measure colonic contractility in conscious germ free (GF) and colonized mice with infusion of tryptamine by enema as well as following colonization of GF with tryptamine producing *E. coli*. The effect of tryptamine on epithelial biology also is determined.

Example 7: Probiotic for Improving Gastrointestinal Epithelial Function

Intestinal microbiota having at least one tryptophan decarboxylase enzyme (e.g., *C. sporogenes* and *R. gnavus*) is given orally (in the form of a probiotic, prebiotic, or symbiotic) to a subject. The subject is evaluated for the presence of the provided bacteria (e.g., probiotic bacteria) in the intestine, production of tryptamine in the intestine, and improved gastrointestinal epithelial function (e.g., colonic contractility). Subjects include GF, HM, 5HTR4 KO, and WT mice. Subjects also include animals (e.g., humans) having a gastrointestinal disorder.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method for treating a gastrointestinal disorder in a human, wherein said method comprises:
   (a) identifying said human as having said gastrointestinal disorder, and
   (b) administering a composition comprising at least one live *Clostridium sporogenes* to said human under conditions wherein gastrointestinal function of said human is improved.

2. The method of claim 1, wherein said gastrointestinal disorder is irritable bowel syndrome.

3. The method of claim 1, wherein said composition comprises at least one bacterial organism comprising exogenous tryptophan decarboxylase activity.

4. The method of claim 3, wherein said at least one bacterial organism comprising exogenous tryptophan decarboxylase activity is *Escherichia coli* or *Bacteroides thetaiotaomicron*.

5. The method of claim 1, wherein said composition is a pill, tablet, or capsule.

6. The method of claim 5, wherein said pill, tablet, or capsule is configured to deliver said live *Clostridium sporogenes* to the intestines of said human.

7. The method of claim 3, wherein said at least one bacterial organism comprises exogenous nucleic acid encoding a polypeptide having tryptophan decarboxylase activity.

8. The method of claim 7, wherein said exogenous nucleic acid encodes a tryptophan decarboxylase derived from *Ruminococcus gnavus*.

\* \* \* \* \*